United States Patent [19]

Szelke et al.

[11] Patent Number: 4,713,445

[45] Date of Patent: Dec. 15, 1987

[54] RENIN INHIBITORS AND TREATMENTS USING THEM

[75] Inventors: Michael Szelke, Ruislip; David M. Jones, Hayes; Allan Hallett, Cheam, all of England

[73] Assignee: Aktiebolaget Hassle, Molndal, Sweden

[21] Appl. No.: 641,639

[22] Filed: Aug. 17, 1984

Related U.S. Application Data

[63] Continuation-in-part of Ser. No. 469,540, Feb. 7, 1983, which is a continuation-in-part of Ser. No. 290,620, Aug. 5, 1981, Pat. No. 4,424,207.

[30] Foreign Application Priority Data

Aug. 19, 1983 [GB] United Kingdom ............... 8322414
Feb. 6, 1984 [EP] European Pat. Off. ......... 84300733.7

[51] Int. Cl.$^4$ ........................... C07K 7/06; C07K 5/10
[52] U.S. Cl. ..................................... 530/330; 530/331
[58] Field of Search ................. 260/112.5 R; 530/330, 530/331

[56] References Cited

U.S. PATENT DOCUMENTS 4,218,474 8/1980 Barnish et al. .................... 424/177
4,424,207 1/1984 Szelke et al. ................. 260/112.5 R

OTHER PUBLICATIONS

IUPAC-IUB Commission on Biological Nomenclature, *J. Biol. Chem.*, vol. 247, 977–983, (1972).

*Primary Examiner*—Delbert R. Phillips
*Attorney, Agent, or Firm*—Larson and Taylor

[57] ABSTRACT

Renin-inhibiting analogues of formula

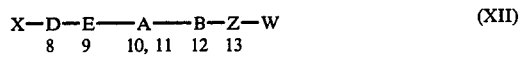

where X and W are terminal groups optionally with further amino acyl residues; D, E, B and Z (of which any one or except with 'reduced' analogues any two may be absent) are aromatic, lipophilic or in the case of E aromatic lipophilic or basic amino acid or amino acid analogue residues; and A is an analogue of a lipophilic or aromatic dipeptide residue wherein the peptide link is replaced by a one- to four-atom carbon or carbon-nitrogen link which as such or in hydrated form is an unhydrolysable tetrahedral analogue of the transition state

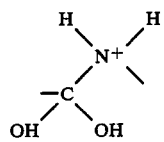

of peptide bond hydrolysis.

35 Claims, No Drawings

RENIN INHIBITORS AND TREATMENTS USING THEM

RELATED CASES

The present application is a c.i.p. of application Ser. No. 469,540 dated Feb. 7, 1983, itself a c.i.p. of application Ser. No. 290,620 dated Aug. 5, 1981 issued as U.S. Pat. No. 4,424,207.

The invention relates to enzyme inhibitors, and particularly renin-inhibiting peptide analogues.

SECTION 1—BACKGROUND AND INVENTION GENERALLY

Renin is a natural enzyme, disorders in relation to which are implicated in many cases of hypertension. It is released into the blood from the kidney, and cleaves from a blood glycoprotein a decapeptide known as angiotensin-I. Circulating angiotensin-I is cleaved in lung, kidney and other tissues to an octapeptide, angiotensin-II, which raises blood pressure both directly by causing arteriolar constriction and indirectly by stimulating release of the sodium-retaining hormone aldosterone from the adrenal gland and thus causing a rise in extracellular fluid volume. The latter effect is caused by angiotensin-II itself or a heptapeptide cleavage product angiotensin-III.

Inhibitors of renin have therefore been sought, with two ends in view, first the provision of a diagnostic agent for identification of cases of hypertension due to renin excess, and secondly the provision of an agent for control of hypertension in such cases.

The present inventors' approach has been to consider the peptide sequence characterising the natural renin substrate at its binding site, and to seek peptide analogues sufficiently similar to bind to the enzyme, in competition with the natural substrate, but sufficiently dissimilar to it to be cleaved slowly or not at all. Such analogues will block the action of the enzyme and attack the hypertension at source.

Renin is specific to a particular bond in the substrate, the N-terminal sequence of which in the horse is for example:

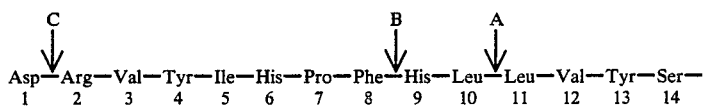

as found by L. T. Skeggs et al J. Exper. Med. 106 439 (1957). Human renin substrate has a different sequence recently discovered by D. A. Tewkesbury et al Biochem. Biophys. Res. Comm. 99 1311 (1981).

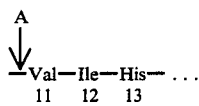

the sequence to the left of the arrow A being as in formula (IA).

Cleavage at A gives angiotensin-I; subsequent cleavage at the Phe-His bond at B gives angiotensin-II; and cleavage subsequently again at the Asp-Arg bond at C gives angiotensin-III.

Peptides similar to certain partial sequences of the substrate have been shown to act as inhibitors of renin in vitro. An example is the tetrapeptide ester (the relation to the substrate residues being indicated by numbering):

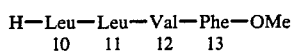

proposed by Kokubu, Nature, 217 456 (1968) but it is inactive in vivo, because of binding to plasma proteins and rapid attack by natural peptidases.

One of the present inventors undertook some years ago a development of Kokubu's work, seeking a renin inhibitor active in vivo, in which analogues of peptides similar to Kokubu's were made but having a methylene imino group -CH$_2$-NH- in place of the peptide link -CO-NH- between the leucine residues. One of these analogues was:

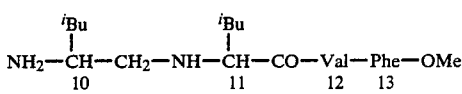

which is the tetrapeptide (I) modified at the Leu-Leu link, leucine of course being

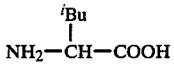

This analogue (III) was the first effective in-vivo inhibitor of renin and was shown to have significant antihypertensive action in Goldblatt hypertensive rats (Parry, Russell and Szelke p. 541 in "Chemistry and Biology of Peptides" Ed. Meienhofer, Ann Arbor Science Publishers 1972). Little or not attention was however paid to the work, which the authors themselves were unable to pursue, in spite of considerable activity in the general field of substrate-based inhibitors for renin, reviewed for exampled by Haber & Burton, Federation Proc. 38 No. 13 2768–2773 (1979).

BASIS OF INVENTION

The invention is based on recognition of the fact that renin has a much greater binding affinity for the transition-state than for the substrate. Non-hydrolysable analogues of the transition-state VI (Table I below) formed at the scissile peptide bond V during hydrolysis of the substrate therefore provide potent enzyme inhibitors.

TABLE I

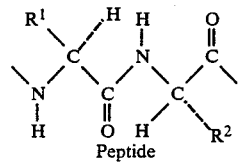

TABLE I-continued

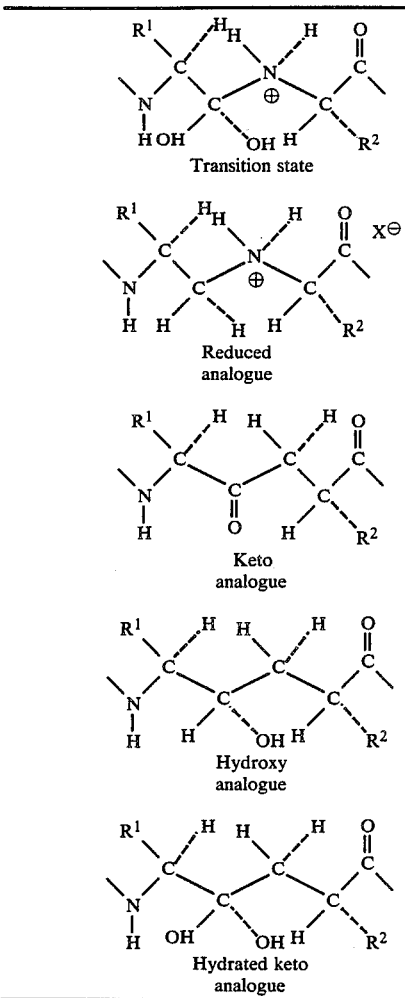

Transition state (VI)

Reduced analogue (VII)

Keto analogue (VIII)

Hydroxy analogue (IX)

Hydrated keto analogue (X)

($R^1$, $R^2$ in this table = amino acid side chain(s))

Thus the inventors have recognised that replacement of the scissile peptide bond V, in a partial sequence or partial sequence analogue of renin substrate, with a 'reduced' analogue VII, a hydroxy analogue IX, the novel 'amino' analogue -$CH(NH_2)$-$CH_2$- (compare IX) or the 'hydrocarbon' analogue -$CH_2$-$CH_2$-(again compare IX) provides such non-hydrolysable analogues. They have also recognised that the 'keto' analogue VIII is capable of reacting with the water molecule present at the active site of aspartic proteinases such as renin to form a tetrahedral hydrate X which is a further non-hydrolysable transition-state analogue. These analogues are also referred to herein as isosteres, and the links they give in the backbone as isosteric links.

Based on structure-activity studies in their own laboratory, and on recent x-ray crystallographic studies (e.g. Blundell et al Nature 304 273 (1983) the inventors have devised novel cyclic structures and other modifications of the substrate sequence including the backbone and N- and C-terminal positions which both increase binding affinity to renin and impart greater stability against breakdown by exo- and endo-peptides in vivo.

In particular, a study of the enzyme-inhibitor complex by computer graphics suggested, and experiments have confirmed, that replacing the hydroxyl function of the 'hydroxy' isostere IX with an amino group capable of carrying a positive charge ('amino' isostere) introduces additional binding through interaction with the negative charge of the aspartic carboxyl functions at the active site of the enzyme. Replacing the hydroxyl group of statine with an amino group to give 'amino-deoxy-statine' has a similar effect.

A particular aspect of the present invention stems from a desire to provide orally active renin inhibitors. On the one hand, a shorter sequence and increased lipophilicity favour absorption from the gut. On the other hand, a longer sequence is usually required to maintain high inhibitory potency and selectivity for renin as opposed to other related proteases in the body. The inventors have found that a balance of these requirements can be achieved by a suitable combination of molecular parameters. For example, the introduction of lipophilic groups can more than offset the loss of potency due to a shortening of the peptide sequence, and at the same time facilitate absorption and increase stability against enzymatic breakdown in vivo (e.g. compare H-270 with H-269, 287 and 288 in Table 2 later herein).

Generally the invention uses a concept of modifying peptide structures related to the peptide sequence at the site of action of renin on the natural substrate, by isosteric substitution at, at least, the site of cleavage. Optionally further there is isosteric substitution or other modification at other positions to increase stability or to modify the properties of the final peptide, for example its solubility under physiological conditions or its resistance to in vivo exopeptidase attack. Such modification may for example be by incorporation of residues other than those of the natural L-amino acids; by protection of the N-terminus with acetyl, pivaloyl, t-butyloxycarbonyl (Boc), benzoyl or other groups; or by conversion of the C-terminal carboxyl to another functional group, e.g. the corresponding alcohol, present as such or in ether or ester form.

INVENTORS' PREVIOUS PATENT APPLICATIONS

In U.S. Pat. No. 4,424,207 compounds are in particular disclosed of the general formula:

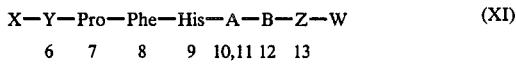

where X and W are various terminal groups, Y (which is optional) is His or other basic or aromatic amino-acyl residue, A is a 'reduced', 'keto', 'hydroxy' or 'hydrocarbon' isostere of a dipeptide, B is a lipophilic amino acyl residue and Z is an aromatic amino acyl residue.

DEFINITIONS

The following definitions apply both to the description of the invention and to the claims unless otherwise specified:

(1) The term 'amino acid' also includes imino acids (e.g. proline, spinacin); furthermore, it includes amino acids of both natural and unnatural origin.

(2) All amino acids may be of either L- or D-configuration unless stated otherwise.

(3) All asymmetric centres may be of either R or S configuration, unless stated otherwise.

(4) The term 'alkyl' includes both branched and straight chain hydrocarbon groups having 1–6 carbon atoms.

(5) The term 'aryl' (abbreviated 'Ar') means phenyl or other (including mono- or bicyclic) aromatic groups, which may be substituted, especially mono-substituted, with one of the following groups, preferably (when phenyl) in the 2- or 4-position F, Cl, Br, I, -CF$_3$, -OH, -OR or -R (R=alkyl).

(6) The term 'aromatic amino acyl' defines amino acid residues having as side-chain an aryl-methyl (ArCH$_2$), imidazol-4-yl-methyl or indol-3-yl-methyl group.

(7) All compounds may be in the free form or as protected derivatives of reactive functional groups such as amino, imino, carboxyl, hydroxyl etc., including peptide nitrogen. Furthermore the compounds may be present in the form of their physiologically acceptable acid addition salts or other derivatives convertible in the body to active form. All salts and derivatives are to be understood in the description and claims to be comprehended in the definitions of the compounds themselves.

Reference to basic and aromatic amino acids above, and to amino acids with lipophilic side chains, in particular includes but is not restricted to the common amino acids of those classes, viz:

| | | |
|---|---|---|
| Basic: | Arginine | |
| | Lysine | |
| | Histidine | |
| Aromatic: | Phenylalanine | |
| | Tyrosine | |
| | Tryptophan | |
| | Histidine | |
| | αNal | } unnatural |
| | βNal | |
| Lipophilic: | Leucine | |
| | Isoleucine | |
| | Valine | |
| | Phenylalanine | |
| | Cyclohexylalanine | } unnatural |
| | Adamantylalanine | |

It should further be noted that symbols X, Y, A etc. in formula (XI) and in (XII), (XIV) and (XV) etc. herein, while generally equivalent where the same symbol is used, are each as defined for their individual formula both in the description and in the claims.

THE PRESENT INVENTION

The present invention is most briefly stated overall as providing renin-inhibiting polypeptide analogues of formula $$X-D-E---A---B-Z-W \quad \text{(XII)}$$
$$\phantom{X-D-E---A---B-Z-W} 8\phantom{-}9\phantom{--}10,11\phantom{-}12\phantom{-}13$$

where X and W are terminal groups; D, E, B and Z, of which any one or, except with 'reduced' analogues, two may be absent, are aromatic, lipophilic or (in the case of E) aromatic, lipophilic or basic amino acid or amino acid analogue residues; and A is an analogue of a lipophilic or aromatic dipeptide residue wherein the peptide link is replaced by a one- to four-atom carbon or carbon-nitrogen link which as such or in hydrated form is an unhydrolysable tetrahedral analogue of the transition state of the peptide bond as given above.

The above compounds may be specifically tetra-, penta- or hexapeptide analogues or for example compounds, without the limitation on two of D, E, B and Z being absent, wherein groups X and/or W themselves contain amino acyl groups such as, for X, Pro or Y-Pro where Y is His or other basic or aromatic amino acyl residue or, for W, Ser or Lys, Arg or other basic amino acyl residue or amino alcohol residue derived therefrom.

The numbering above and in other formulae herein indicates the relation to the natural renin substrate sequence, though without limitation of the invention.

The invention extends further to sundry novel dipeptide analogues with the replaced peptide link, both as such and when used in renin-inhibitory or other peptide analogues of any length, particularly 'amino', 'cyclic' and 'aminostatine' compounds as referred to herein.

Finally the invention extends to the new compound 3-amino-3-deoxy-statine ('amino-statine')

which is 3,4-diamino-6-methyl-heptanoic acid.

SECTION 2—A DETAILED ASPECT

In more detail, the compounds of one aspect of the present invention, showing desirable renin inhibitory action, are of the general formula:

$$X-Y-Pro-Phe-His---A---B-Z-W \quad \text{(V)}$$
$$\phantom{X-Y-}6\phantom{-Pro-}7\phantom{-Phe-}8\phantom{-His}9\phantom{---}10,11\phantom{-A--}12\phantom{-B-}13$$

or the partial sequences:

| | |
|---|---|
| X—A—B—Z—W | (V)(i) |
| X—His—A—B—Z—W | (V)(ii) |
| X—Phe—His—A—B—Z—W | (V)(iii) |
| X—Pro—Phe—His—A—B—Z—W | (V)(iv) | where Pro, Phe and His may be in the substituted form; e.g. Pro by OH preferably at the 4-position, Phe by OH F Cl Br or Me preferably at the 4-position, His by Me; or Phe is replaced by pGlu, Phe by Tyr or His by spinacin.

X=H; or an acyl or other N-protecting group e.g. acetyl, pivaloyl, t-butyloxycarbonyl (Boc), benzoyl or lower alkyl (primarily C$_1$-C$_5$); or an L- or D-aminoacyl residue, which may itself be N-protected similarly and in particular may be Gly or D- or L-Pro, Val or Ile;

Y=D- or L-His or other D- or L-basic or aromatic amino-acyl residue, or is absent;

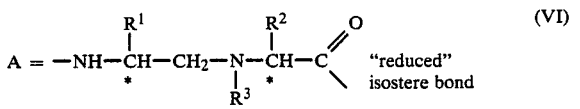

"reduced" isostere bond (VI)

or

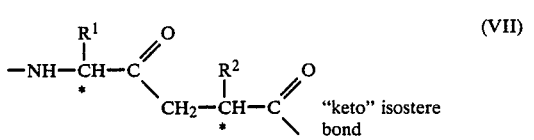

"keto" isostere bond (VII)

or

-continued

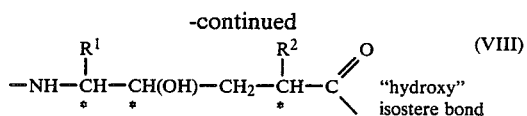 "hydroxy" isostere bond (VIII)

or

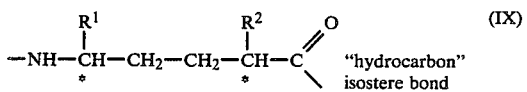 "hydrocarbon" isostere bond (IX)

or

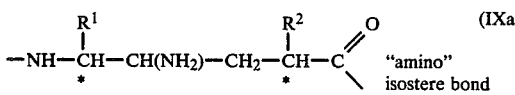 "amino" isostere bond (IXa)

or compounds with any of the above five isostere bonds and, further, cyclised between the nitrogen adjacent to the $R^1$-bearing carbon and the methylene adjacent to the $R^2$-bearing carbon by a group $-CH_2-(CH_2)_n$, $-(CH_2)_n-CO-$ or $-CO-(CH_2)_n$ where $n=0$ to 3 where the configuration at asymmetric centres * is either R or S, where in VIII the hydroxy group may be present as such or protected in ether $-OR^4$ or ester

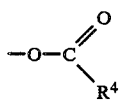

form where
$R^4$ is as given under W below and where
$R^1$ and $R^2$, the same or different$=^i$Pro (isopropyl), $^i$Bu (iosbutyl), Bzl (benzyl) or other amino-acid side chain preferably lipophilic or aromatic
$R^3=$-H; lower alkyl ($C_1$-$C_5$); or t-butyloxycarbonyl, benzyloxycarbonyl as such or ring substituted, $-SO_2Ph$, $-SO_2-C_6H_4CH_3(p)$, formyl or other N-protecting group including lower acyl $C_1$-$C_5$ generally;
B=D- or L-Val Leu or Ile or other D- or L-lipophilic amino-acyl residue;
Z=D- or L-Tyr, Phe, His or other L- or D-aromatic amino-acyl residue; and
W=(i)-OH as such or in protected ester form as $-OR^4$ where $R^4=$lower alkyl primarily $C_1$-$C_5$ and particularly $^t$Bu, or cycloalkyl primarily $C_3$-$C_7$, or Bzl, or other ester forming group; or (ii) $-NH_2$ as such or in protected amide form as $-NHR^5$ or $-N(R^5)_2$ (where $R^5=$an N-protecting or other substituent group e.g. lower alkyl as for $R^4$ and $(R^5)_2=$two such or e.g. cycloalkyl, primarily $C_3$-$C_7$) or as $-NH-(CH_2)_n-Q$ or $-NR^5-(CH_2)_n-Q$ (where $n=2$ to 6 and $Q=NH_2$ or

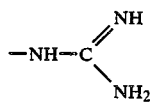

and wherein any of the hydrogens attached to nitrogen may be substituted by $R^5$ or $(R^5)_2$); or (iii) an L- or D-serine or D- or L-lysine, arginine or other basic amino-acyl residue as such or in amide form substituted amide form or ester form e.g. containing a group or groups as given for $R^4$ and $R^5$ above as the case may be; or (iv) an amino alcohol residue derived therefrom as such or protected in ester or ether form e.g. containing a group as given for $R^4$ above or
Z+W=an alcohol derived from L- or D-Tyr, Phe, His or other L- or D-aromatic amino-acyl residue as such or protected in ester or ether form as above;
such polypeptide being in the above form or modified by isosteric replacement of one or more remaining peptide bonds e.g. by reduced, $-CH_2-NH-$, keto,

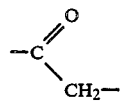

hydroxy, $-CH(OH)-CH_2-$, or hydrocarbon, $-CH_2-CH_2-$ isosteric links as set out above for A and further being in free form or in protected form at one or more remaining amino or amide (including peptide) nitrogen, carboxyl, hydroxy or other reactive groups, or in salt form at amino imidazole or carboxyl groups in particular as their physiologically acceptable acid addition salt at basic centres.

The above compounds may in particular be those related to the substrate sequence in the horse (B=Val at position 12) or those related to the substrate sequence in man (B=Ile at position 12). Particular groups of these compounds are set out in claims 18 and 19 respectively herein, as formulae VA and VB to which reference may be made but which are not repeated at this point.

The numbering of residues in formulae (V), (VA) and (VB) shows the correspondence with the renin substrates themselves, but without limitation of the generality of the formulae.

Where a peptide bond in addition to that corresponding to the Leu-Leu or Leu-Val bond in the natural renin substrate is isosterically substituted, the 7, 8 and 8, 9 positions i.e. the Pro-Phe and Phe-His bonds in formula V etc. are preferred, or possibly both of these positions, and it is further preferred that the substitution should be

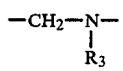 (X)

where $R_3$ is as set out above. The alternative isosteric substitutions set out herein may however be used.

Protective or substituent groupings as mentioned above may be any of these known in the polypeptide art, amply disclosed in the literature and not requiring discussion at length here. Generally the selection of the groups is according to their function, some being primarily intended to protect against undesired reaction during synthetic procedures while the N- and C-terminal substituents are for example directed against the attack of exopeptidases on the final compounds or to increase their solubility and hence physiological acceptability. All these functions are generally within the term "protective group" or the like used herein, including the claims.

It is in particular possible for one or more remaining peptide bonds in the compounds of formula (V) etc., (VA) or (VB) to be N-substituted with protective groups.

For use in the invention hydroxy or keto isosteres of dipeptides may be made by a method wherein a derivative of a halohydrin preferably a bromohydrin or haloketone preferably a bromoketone

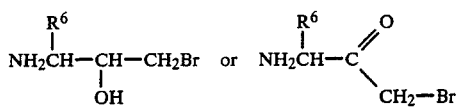

wherein $R^6$ is an amino acid side chain and the $NH_2$ and OH groups are in protected form is subjected to an alkylation procedure to attach a group

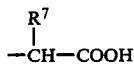

and gives the desired isostere as such or in protected form, $R^7$ being the same or a different amino acid side chain.

In particular the alkylation procedure may be (i) by reaction with an alkali metal carboxylic acid derivative preferably a lithium derivative

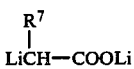

where $R^7$ is as above.

(ii) by reaction with an alkali metal malonic ester derivative preferably a sodium derivative

where $R^8$ is an esterifying group and a halide preferably an iodide

 $R^7$-I where $R^7$ is as above to give intermediate

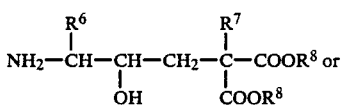

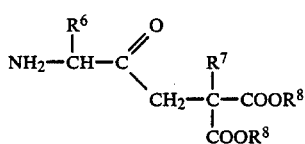

in protected form which intermediate is then decarboxylated and if desired deprotected to give the desired isostere

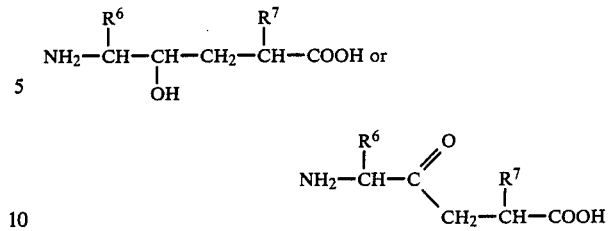

as such or in protected form.

The hydroxy isosteres so produced may further be oxidised to the corresponding keto isosteres.

In particular the methods may be applied to the production of a hydroxy dipeptide isostere of the formula

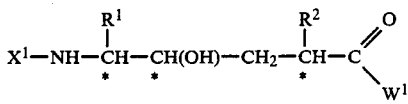

or the corresponding keto isosteres, where the significance of *, $X^1$ and $W^1$ is as above except that $X^1$ and $W^1$ do not represent amino-acyl.

The dipeptide isosteres given by all these methods may be incorporated in higher peptide analogues by the methods herein described or by the methods of peptide synthesis as generally known in the art.

Specific analogues within the present aspect of the invention, all as such or in protected form, are

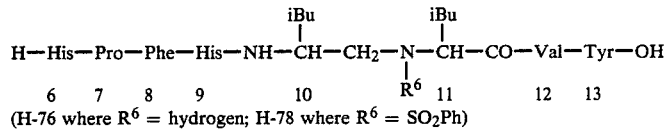

(H-76 where $R^6$ = hydrogen; H-78 where $R^6$ = $SO_2Ph$)

and the corresponding analogue (H-77) with $R^6$=hydrogen and D-His at position 6. A further analogue, with the same methylene-imino isosteric replacement of a Leu-Leu peptide bond, is:

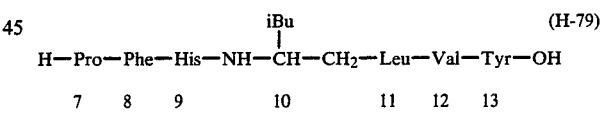

(H-79)

Further analogues within formula (VA) are given in the present disclosure in Examples VI to IX, XI and XII. Analogues within formula (VB) are given in Examples V and X.

SECTION 3—A FURTHER DETAILED ASPECT

In a further detailed aspect the compounds of the present invention are of the general formula

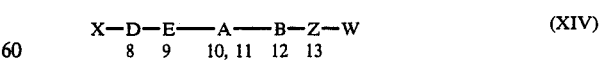

where optionally Y-Pro is inserted between X and D, Y being D- or L-His or other D- or L-basic or aromatic amino acyl residue and Pro being as such or substituted by OH preferably at the 4-position or replaced by pGlu and/or W is serine or L- or D-lysine, arginine or other basic amino-acyl residue as such or in amide form, substituted amide form or ester form e.g. containing a group or groups as given for $R^4$ and $R^5$ above as the case may be; or an amino alcohol residue derived therefrom as duch as protected in ester or ether form e.g. containing a group as given for $R^4$ above and where X=H or an N-protecting group or groups, e.g. as follows:

(a) $R^3$—$(CH_2)_n$—, where n = 0–4, or
(b) $R^3$—CO— or
(c) $R^3$—O—CO— or
(d) $R^3$—$(CH_2)_n$—CO— or
(e) $R^3$—$(CH_2)_n$—O—CO or  } where n = 0–5
(f) $R^3$—O—$(CH_2)_n$—CO— or
(g) $R^3SO_2$— or
(h) $(R^3)_2$—N—CO—

In (a)-(h), $R^3$ =
  (i) H (except in (c)) or
  (ii) alkyl (e.g. t-butyl) or
  (iii) cycloalkyl $C_{3-7}$
    (e.g. cyclohexyl) or
  (iv) bicycloalkyl or tricycloalkyl
    $C_{7-12}$ (e.g. isobornyl or
    adamantyl) or
  (v) aryl (e.g. phenyl) or aryl
    alkyl D = (a) absent
  (b) aromatic amino acyl (e.g. Phe, αNal, βNal, Tyr, His, Trp)
  (c) lipophilic amino acyl (e.g. cyclohexyl-alanyl)
  (with (b) and (c) either as such or reduced at carbonyl)

E = (a) absent or
  (b) aromatic amino acyl (e.g. His, Phe, Tyr, Trp) or
  (c) lipophilic or basic amino acyl (e.g. 2-amino-butyryl, α, δ-diaminovaleryl), (b) and (c) being as such or $N^\alpha$-alkylated and/or reduced at carbonyl A = (a) 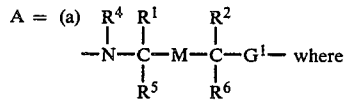

$R^4$, $R^5$ and $R^6$ the same or different =
  (i) H or
  (ii) alkyl (e.g. Me) or
  (iii) —$(CH_2)_n$—OH or —$(CH_2)_n$—$NH_2$
    when n = 2, 3, 4

$G^1$ (and $G^2$ appearing below) =
  (i) —$CH_2$—$(CH_2)_n$— or
  (ii) —$(CH_2)_n$—CO— or  } where n = 0–3
  (iii) —CO—$(CH_2)_n$—

$R^1$ and $R^2$, the same or different =
  (i) alkyl (e.g. $^iPr$, $^iBu$, $^sBu$) or
  (ii) $ArCH_2$ or
  (iii) other lipophilic group (e.g. cyclohexyl-methyl) or
  (iv) H (especially for $R^2$)

M = (i) —CH(OH)—$(CH_2)_n$— or
  (ii) —CH($NH_2$)—$(CH_2)_n$— or
  (iii) —$CH_2$—$(CH_2)_n$— or
  (iv) —CO—$(CH_2)_n$— or  } where n = 0–2
  (v) —$(CH_2)_n$—N($R^7$)—, where
    $R^7$ = X or
  (vi) —CH($NH_2$)—$(CH_2)_n$—CO—NH— with the provisos (I) that when M = (i), (iii) or (iv) and n = 1 then two three or four, and when M = (v) and n = 1 then three or four, or D, E, B and Z are present and preferably that when M = (i), (iii) or (iv) then two, three or four and when M = (v) then three or four of said residues are present
(II) when M = (i), (ii) or (iv) then $R^5$ and $R^6$ are H when M = (iii) or (v) then if one of $R^4$, $R^5$, $R^6$ and $R^7$ is said group —$(CH_2)_n$—OH or —$(CH_2)_n$—$NH_2$ the others, the same or different, are H or alkyl -continued (b) 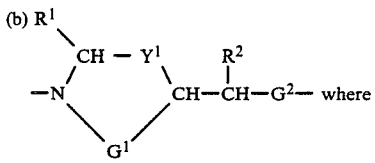

$R^1$, $R^2$ and $G^1$, $G^2$, the same or different, are as defined above and $Y^1$ =
  (i) —CO— or
  (ii) —$CH_2$— or
  (iii) —CH(OH)— or
  (iv) —CH($NH_2$)— or
  (v) —$CH_2$—$NR^3$—($R^3$ as above)

B = (a) absent or
  (b) lipophilic or aromatic amino acyl (e.g. Val, Leu, Ile, Phe) either as such or Nα-alkylated and/or reduced at carbonyl Z = (a) absent or
  (b) aromatic amino acyl (e.g. His, Phe, Tyr) or
  (c) lipophilic amino acyl (e.g. cyclohexyl-alanyl),
  (b) and (c) being either as such or Nα-alkylated and/or reduced at carbonyl, W = (a) —OH or other terminal group including those set out for W in general formula XV
  (b) —$OR^3$
  (c) —$NH_2$, —$NHR^3$, —$NR_2^3$  } $R^3$ as above (d) —N⟩ where N is part of a heterocyclic ring, preferably 5- or 6-membered, containing 1–3 heteroatoms (N, O or S) and of any degree of saturation and optionally substituted with $R^3$— or $R^3CH_2$— groups at one or more positions ($R^3$ as above)

or
Z-W = $QCH_2$ 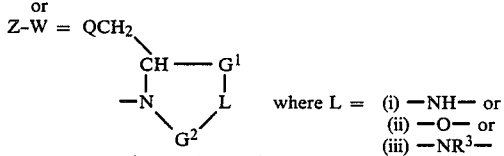 where L = (i) —NH— or
  (ii) —O— or
  (iii) —$NR^3$— and $R^3$ and $G^1$ and $G^2$, the same or different, are as defined above and

Q = (i) H or
  (ii) $C_{1-4}$ alkyl or
  (iii) aryl or
  (iv) imidazol-4-yl- or indol-3-yl together with compounds in which, when one or more of the peptide bonds of the chain is represented by a 'reduced' isostere, the N atom of such isostere and the preceding or succeeding N atom in the chain are linked by a moiety as defined for $G^1$ and giving a five or six membered ring, and together further with compounds in which (except when M=(i), (iii), (iv) or (v), at least for n=1) the above residues are present with further, N- or C-terminal, aminoacyl or aminoacyl analogue residue(s), particularly Pro or J-Pro interposed between X and D, J being His or other basic or aromatic aminoacyl residue.

In the above, compounds where, in M, n=1 are preferred. Of the isosteric links, the hydroxy ones are of particular value as giving high bonding affinity, from their close relation to the transition stage of the scissile (peptide) bond. Other important isosteric links are the 'amino', 'cyclised' and 'aminostatine' links where respectively A is (a) and M=(ii); A is (b); and A is (a) and M=(vi).

These compounds may, further, be in the form shown or modified by replacement of one or more remaining peptide bonds by analogues M, e.g. reduced -$CH_2NH$-, keto -CO-CH$_2$-, hydroxy -CH(OH)-CH$_2$, amino -CH(NH$_2$)-CH$_2$- or hydrocarbon -CH$_2$-CH$_2$- isosteric linkages. They may be in the free form or as protected derivatives of reactive functional groups such as amino, imino, carboxyl, hydroxyl etc., including peptide nitrogen. Furthermore the compounds may be present in the form of their physiologically acceptable acid addition salts or other de ivatives convertible in the body to active form. All salts and derivatives are to be understood in the description and claims to be comprehended in the definitions of the compounds themselves.

Particular compounds of this aspect of the invention, showing desirable renin inhibitory action, are of the general formula:

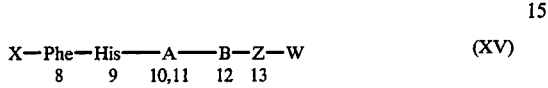

(XV)

where Phe and His are optional (but are not both absent when A has the 'reduced' link below) and may further be in substituted form e.g. Phe by OH F Cl Br or Me, preferably at the 4-position, or His by Me; or Phe is replaced by Tyr, or His by spinacin X=H; or an acyl or other N-protecting group, e.g. acetyl, pivaloyl, t-butyloxycarbonyl (Boc), benzoyl or lower alkyl (primarily C$_1$-C$_5$); or an L- or D-amino-acyl residue, which may itself be N-protected similarly and in particular may be Gly or D- or L-Pro, Val or Ile

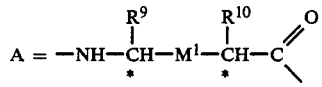

where M$^1$ is as M above or particularly a 'reduced'

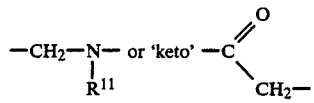

or 'hydroxy' -CH(OH)-CH$_2$-, or 'hydrocarbon' -CH$_2$-CH$_2$- isostere bond where the configuration at asymmetric centres is either R or S, where in the hydroxy isostere the hydroxy group may be present as such or protected in ether -OR$^{12}$ or ester

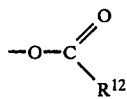

form where R$^{12}$ is as given under W below and where R$^9$ and R$^{10}$, the same or different=$^i$Pro (isopropyl), $^i$Bu (isobutyl), Bzl (benzyl) or other amino-acid side chain preferably lipophilic or aromatic;

R$^{11}$=-H or an N-protecting group such as lower alkyl or lower acyl (C$_1$-C$_5$), or t-butyloxycarbonyl or benzyloxycarbonyl as such or ring substituted, or aryl sulphonyl e.g. -SO$_2$Ph or -SO$_2$-C$_6$H$_4$CH$_3$(p), or formyl;

B=D- or L-Val Leu or Ile or other D- or L-lipophilic amino-acyl residue;

Z=D- or L-Tyr, Phe, His or other L- or D-aromatic amino-acyl residue; and

W=

(i) -OH as such or in protected ester form as -OR$^{12}$ where R$^{12}$=lower alkyl primarily C$_1$-C$_5$ and particularly $^t$Bu, or cycloalkyl primarily C$_3$-C$_7$, or other ester forming group; or (ii) -NH$_2$ as such or in protected amide form as -NHR$^{13}$ or -N(R$^{13}$)$_2$ (where R$^{13}$=an N-protecting or other substituent group e.g. lower alkyl as for R$^{12}$, and (R$^{13}$)$_2$=two such or e.g. cycloalkyl, primarily C$_3$-C$_7$) or as -NH-(CH$_2$)$_n$-Q$^1$ or -NR$^{13}$-(CH$_2$)$_n$-Q$^1$ (where n=2 to 6 and Q$^1$=NH$_2$ or

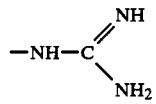

and wherein any of the hydrogens attached to nitrogen may be substituted by R$^{13}$ or (R$^{13}$)$_2$); or (iii) an L- or D-serine or L- or D-lysine, arginine or other basic amino-acyl residue as such or in amide form, substituted amide form or ester form e.g. containing a group or groups as given for R$^{12}$ and R$^{13}$ above as the case may be; or (iv) an amino alcohol residue derived therefrom as such or protected in ester or ether form e.g. containing a group as given for R$^{12}$ above; or Z+W=an alcohol derived from L- or D-Tyr, Phe, His or other L- or D-aromatic amino-acyl residue as such or protected in ester or ether form as above.

As with the previously set out general formulae the compounds may be in the above form or modified by isosteric replacement of one or more retaining peptide bonds e.g. by reduced -CH$_2$-NH-, keto

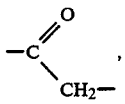

hydroxy -CH(OH)-CH$_2$-, hydrocarbon -CH$_2$-CH$_2$- or other analogue links M and further being in free form or in protected form at one or more remaining amino or amide (including peptide) nitrogen, carboxyl, hydroxy or other reactive groups, or in salt form at amino imidazole or carboxyl groups in particular as their physiologically acceptable acid addition salts at basic centres.

Protective or substituent groupings as mentioned above may be any of these known in the polypeptide art, amply disclosed in the literature and not requiring discussion at length here. Generally the selection of the groups is according to their function, some being primarily intended to protect against undesired reaction during synthetic procedures while the N- and C-terminal substituents are for example directed against the attack of exopeptidases on the final compounds or to increase their solubility and hence physiological acceptability. All these functions are generally within the term "protective group" or the like used in the description and claims herein.

SECTION 4—DIAGNOSIS AND TREATMENT

The invention further lies (a) in a diagnostic test aimed at establishing the significance of renin as a causative or contributing factor in hypertension or hyperaldosteronism, and a surgical prognostic test for renovascular hypertension, in which there is administered a renin-inhibiting analogue according to the invention and blood pressure is monitored, and (b) in the treatment of various forms of hypertension, particularly those forms associated with increased activity of the renin-angiotensin system, in which there is administered a renin inhibiting analogue according to the invention.

The long and short term response of blood pressure to renin inhibitors is predictive of surgical outcome. In all cases single and repeated doses and any conventional form of pharmaceutical composition may be used, for administration by intranasal or oral route, injection, or any other means as convenient. Amounts may for example be 0.001 to 10 mg/kg body weight (calculated as free base) daily more usually 0.01 to 1 mg, according to the potency of the analogue and the severity of the condition. Dosage unit compositions may contain such amounts or submultiples thereof to make up the daily dose.

SECTION 5—SPECIFIC DESCRIPTION

In the following specific description individual schemes have numbering of the compounds not necessarily related to that of other schemes.

PART A

SYNTHETIC METHODS FOR DIPEPTIDE ANALOGUES

The inventors have developed synthetic methods for the isosteric replacement of the peptide bond -CO-NH- with alternative groups, specifically -CH$_2$-NH- (reduced), -CH$_2$CH$_2$- (hydrocarbon),

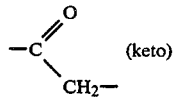

and -CH(OH)-CH$_2$- (hydroxy) isosteres (see, e.g. Szelke, et al, pp. 57–70 in "Molecular Endocrinology" Vol. 1, Editors: MacIntyre and Szelke, Elsevier, Amsterdam 1977, and Hudson, Sharpe and Szelke, U.S. Pat. No. 4,198,398 "Enkephalin Analogues").

Reference may be made to these publications for general discussion of such isosteric replacement. However a sequence for the preparation in particular of the reduced isostere of leucyl leucine for incorporation in the analogues disclosed herein is for example (scheme 1):

Synthesis of the protected
reduced isostere of L-leucyl-L-leucine

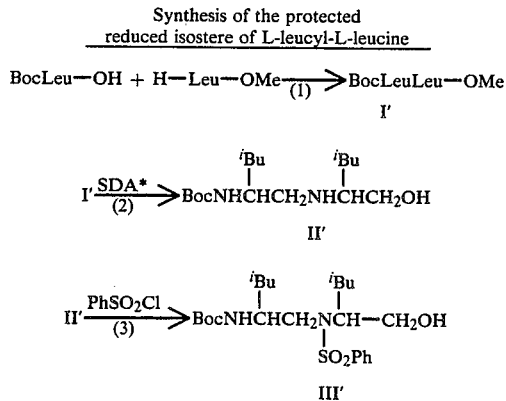

-continued
Synthesis of the protected
reduced isostere of L-leucyl-L-leucine

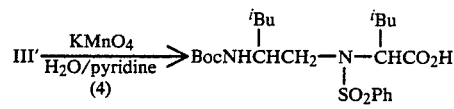

°Sodium di(methoxyethoxy) aluminium hydride (1) Boc-Leucyl-leucine methyl ester

The dipeptide I' was prepared from Boc-leucine.H$_2$O (27.5 g, 0.11 mole) and leucine methyl ester. HCl (20 g, 0.11 mole) by mixed anhydride coupling using N-methyl morpholine and isobutylchloroformate. After a standard work-up procedure the dipeptide I' was obtained as white needles, 35.0 g (88%) from EtOAc/petrol bpt 40°–60°, m.p. 132°–133°

(2) Preparation of compound II'

The dipeptide I' (7.2 g, 20 mmole) was dissolved in benzene (120 ml, Na-dried). A solution of sodium dihydro-bis-(2-methoxyethoxy)aluminate (SDA, 70% in toluene, 41 ml) was added slowly with cooling. After addition, the solution was refluxed for ½ hr, cooled and poured into 0.5M ice-cold citric acid solution. At pH 2.5 the aqueous solution was extracted with ether (4X) and the combined extracts were discarded. The pH was adjusted to 9 with Na$_2$CO$_3$ solution and the aqueous solution was saturated with sodium chloride. Extraction with ether (4×), followed by drying (Na$_2$SO$_4$) of the combined organic phases, evaporation and crystallisation from petrol (40°–60°) at −20° gave the reduced dipeptide II': 5.1 g (78%) as white needles.
m.p. 59°–60°.

Nmr (CDCl$_3$) 9.05–9.15 (12H, d, 4×CH$_3$) 8.75 (6H, m, 2×(CH$_3$)$_2$CH-CH$_2$); 8.55 (9H, s, (CH$_3$)$_3$CO); 7.35 (5H, m, CH$_2$NH, CH$_2$OH); 6.05–6.85 (3H, m, 2×α-CH and CH$_2$OH); 5.3 (1H, d, Boc NH-).

(3) Protection of compound II' with benzenesulphonyl

The reduced compound II' (11.0 g, 34.7 mmole) in dioxan (100 ml) was added to a solution of KHCO$_3$ (21 g., 6 equiv.) in H$_2$O (100 ml). This mixture was cooled in ice and benzene-sulphonyl chloride (9.0 ml, 2 equiv.) added in dioxan (25 ml) with vigorous stirring. Stirred at 22° overnight. Poured into ether, washed with 2N NH$_4$OH (4×), H$_2$O (1×) 0.5M citric acid (2× to remove any unsulphonated material), H$_2$O (1×).

The protected compound III' was obtained as an oil. Nmr spectroscopy showed the presence of one benzenesulphonyl group. This material was used without further purification in the next stage:

(4) Oxidation of compound III'

The material from the preceding preparation was taken up in pyridine (50 ml), cooled in ice and KMnO$_4$ (11.0 g 70 mmole) in H$_2$O (50 ml) and pyridine (100 ml) added. Stirred for 42 hrs at 20°. The MnO$_2$ precipitate was removed and the filtrate diluted with citric acid solution until acidic. Ether extraction at pH 5 removed product and starting material. The product IV' was obtained by (i) NaHCO$_3$ extraction—to remove strongly acidic by-products (ii) extracted with 30% v/v 0.880 ammonia solution (6×). The ammonia washes contained essentially pure IV'. Starting material remaining in the ether was re-oxidised for 42 hrs and worked-up as above.

The total amount of IV' (isolated by acidifying the ammonia washes and extracting with CHCl₃) obtained was 2.34 g (20% based on II').

The material was a colourless foam RF 0.41 by TLC on silica in benzene-dioxan-acetic acid (95:25:4).

Nmr (CDCl₃): 8.9–9.3 (12H, m, 4×C$\underline{H}_3$); 8.2.14 8.8 (15H, m, (C$\underline{H}_3$)$_3$CO and 2× (CH$_3$)$_2$C$\underline{H}$-C$\underline{H}_2$); 5.4–7.0 (4H, m, 2×α-C$\underline{H}$ and -C$\underline{H}_2$-N-); 2.0 and 2.4 (5H, m, C$_6$$\underline{H}_5$SO$_2$), 1.2 (1H, br.s, CO$_2$$\underline{H}$).

Alternatively, the reduced Leu-Leu analogue IV may be synthesized by the following method (scheme 2):

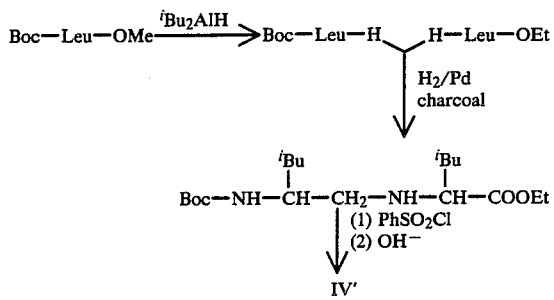

The following is a synthetic method for a reduced Leu-Val isotere by a preferred route (scheme 3):

Synthesis of the Protected
Reduced Isostere of L-Leucyl-L-Valine

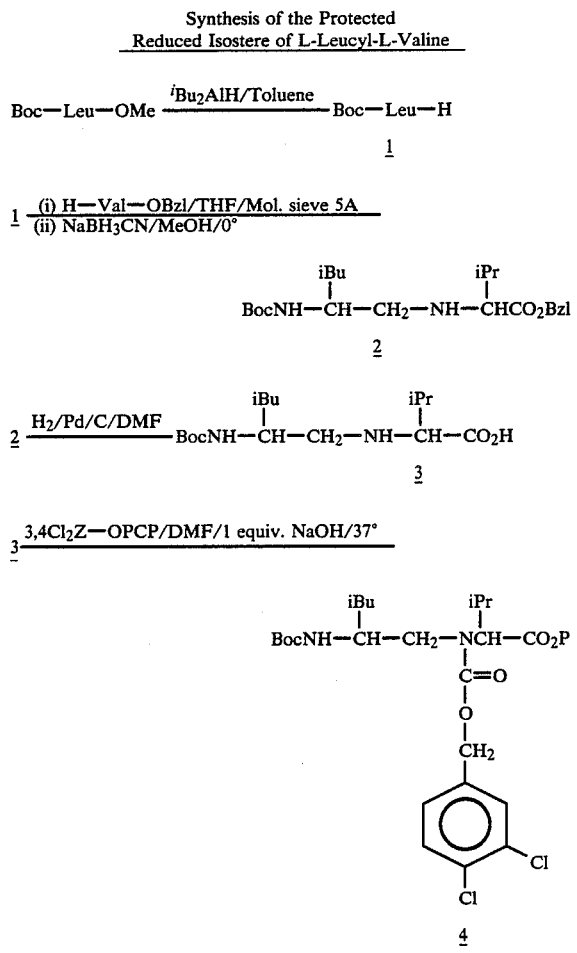

(1) Boc-L-Leucinal, 1

Boc-L-Leucine methyl ester (22.7 g, 90 mmoles) in dry toluene (250 ml) under N₂ was cooled to −78° and 25% di-isobutylaluminium hydride in toluene (130 ml, 225 mmoles) were added over 25 mins. keeping the temperature under −70°. The mixture was stirred for 15 mins. at −78° after completion of the addition, then MeOH (10 ml) was added cautiously. When effervescence ceased the mixture was poured into an ice-cold solution of Rochelle salt (100 ml of saturated solution +600 ml H₂O). This mixture was shaken until an extractable solution was obtained. The toluene was separated and the aqueous phase re-extracted with ether (2×300 ml). Toluene and ether extracts were combined and dried (Na₂SO₄). The resulting oil was passed rapidly through a pad of silica gel in 15% EtOAc/petrol 40°-60°. The crude aldehyde was obtained as an oil, weight 18.68 g. Nmr showed aldehyde content to be b 85%, therefore yield of aldehyde: 15.9 g (83%).

Nmr (CDCl₃), τ: 0.45 (1H, s, C$\underline{H}$O); 4.87 (H, br.d., Boc N$\underline{H}$): 5.83 (1H, br.m., NH-C$\underline{H}$CHO); 8.43–8.93 (12H, m, (CH$_3$)$_3$C, (CH$_3$)$_2$CH.C$\underline{H}_2$); 9.0 and 9.1 (12H, 2×d, (C$\underline{H}_3$)$_2$CH).

TLC: (solvent 30% EtOAc/petrol 60°-80°), Rf=0.43.

(2) Boc-L-Leucyl-L-valine benzyl ester reduced isostere, 2

L-Valine-OBzl (10 mmoles, from EtOAc/1N NaHCO₃ partition of 3.8 g of p-toluene sulphonate salt) and Boc-L-Leucinal (2.54 g, 10 mmole aldehyde content) in dry tetrahydrofuran (20 ml) stood over 5 Å molecular sieve (10 g) overnight. Sodium cyanoborohydride (630 mg, 10 mmoles) in MeOH (3 ml) was added with cooling, then left at room temperature for 30 mins. The mixture was diluted with methylene chloride (100 ml), filtered and evaporated to dryness. The residue was passed down a silica column in 20% EtOAc/petrol (60°-80°) to remove polar impurities. Isostere containing factions were combined. Crystallisation from petrol 60°-80° at −20° gave large clusters of needles, 1.52 g (38%) m.p.

τ: 2.65 (5H, s, OC$\underline{H}_2$C$_6$H$_5$); 6.35 (1H, m, N$\underline{H}$CHCO$_2$Bzl); 7.05 (1H, m, N$\underline{H}$-CHCH$_2$); 7.45 (2H, m, -C$\underline{H}_2$NH-); 8.25–8.90 (13H, m, (CH$_3$)$_3$CO-.) (CH$_3$)$_2$C$\underline{H}$CH$_2$ and (CH$_3$)$_2$C$\underline{H}$-); 9.05 and 9.15 (12H, 2×s, 2× (C$\underline{H}_3$)$_2$CH).

TLC: (Solvent: 30% EtOAc/petrol 60°/80°) Rf=0.39.

(3) N-(2S)-t-Butyloxycarbonylamino-4-methylpentyl, N-(3,4-dichlorobenzyloxycarbonyl)-L-valine, 4

Boc-L-Leucyl-L-valine, benzyl ester-reduced-isostere (1.5 g 3.68 mmoles) in dimethylformamide (60 ml) was hydrogenated at STP over 5% Pd/C (150 mg). After 3½ hrs. the colloidal solution was flushed with nitrogen and 1M NaOH (3.8 ml, 1.05 equiv.) was added followed by 3,4-dichlorobenzyl pentachlorophenyl carbonate (1.92 g, 4.07 mmoles). The mixture was kept at 50° in a stoppered flask for 24 hrs. and then evaporated to dryness. EtOAc was added and the Pd/C filtered off. The EtOAc solution was washed with 1M citric acid (2×), H₂O (1×), brine (1×), and dried (Na₂SO₄).

The crude isostere 4 was chromatographed on silica-gel (Merck Keiselgel 60, 40–63 m) eluting with 2% MeOH/CHCl₃ to give the title compound as a colourless oil.

Nmr(CDCl₃), τ: 2.5–2.9(3H, m, $C_6Cl_2H_3$); 3.3–3.8 (2H, br, BocN$\underline{H}$ and CO₂$\underline{H}$); 4.85 and 4.95 (2H, 2×s, OC$\underline{H}_2$-$C_6Cl_2H_3$); 5.5–6.3(2H, m, NHC$\underline{H}$CH₂ and -NC$\underline{H}$CO₂H); 6.5–7.2 (2H br, 2×d, CHC$\underline{H}_2$N-); 8.2–8.9 (13H, m, (CH₃)₃CO, (CH₃)₂CHC$\underline{H}_2$ and (CH₃)₂C$\underline{H}$-); 8.8–9.4 (12H, m, 2× (C$\underline{H}_3$)₂CH).

TLC: (solvent 5% MeOH/CHCl₃) Rf=0.32.

The reaction scheme below, also suitable for other hydroxy dipeptide analogues, was used to synthesise an N-terminal and hydroxy-group protected Leu-Leu hydroxy isostere 18 (scheme 4):

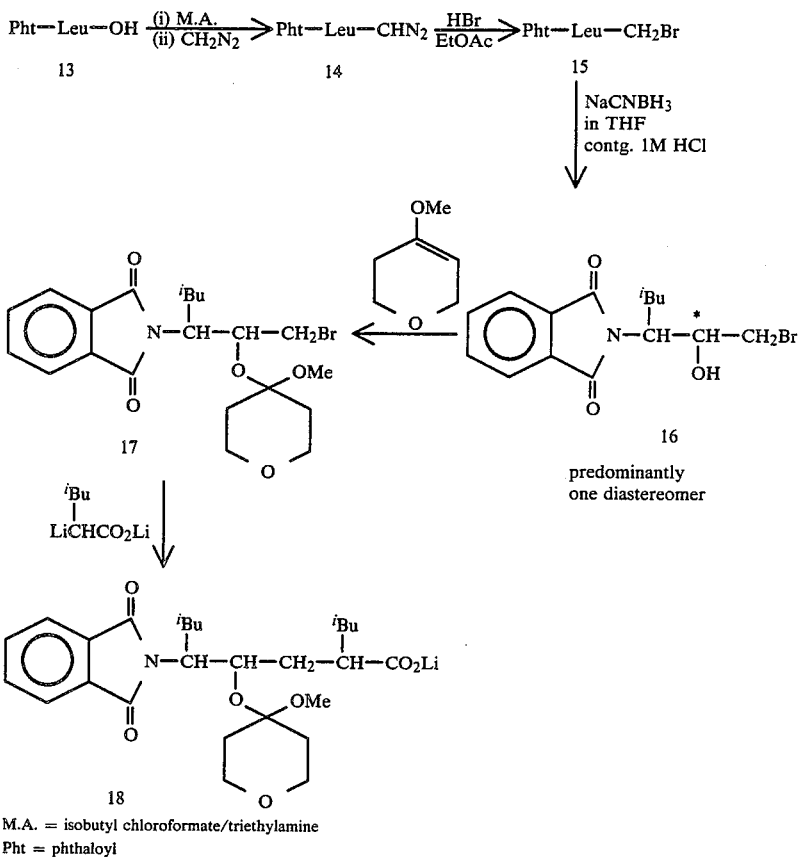

M.A. = isobutyl chloroformate/triethylamine
Pht = phthaloyl

This dipeptide analogue is suitable for incorporation into polypeptide analogues, see Example XIII herein.

The alternative and preferred reaction scheme below, also suitable for other dipeptide hydroxy isosteres was used to synthesise an N-terminal and hydroxy-group protected Leu-Val hydroxy isostere 23 (scheme 5):

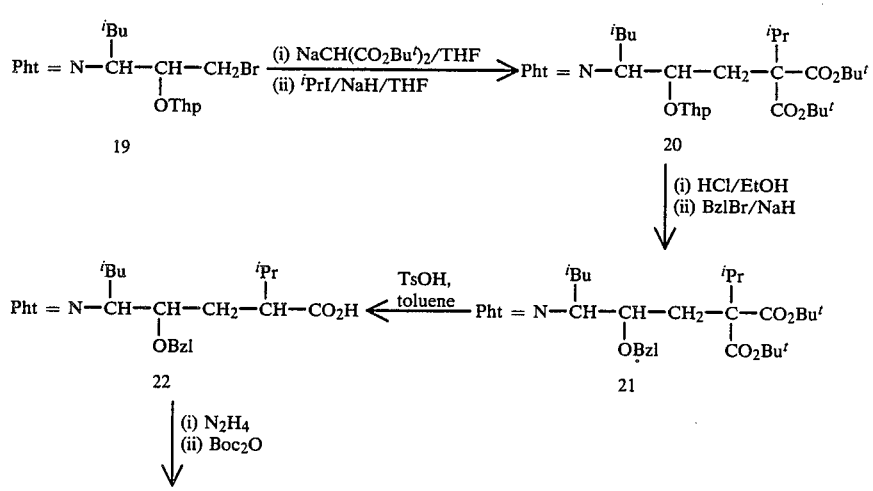

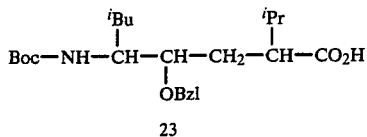

Pht = Phthaloyl,
Thp = Tetrahydropyranyl

In the above scheme the protected bromohydrin 19 is obtained in the same way as the corresponding intermediate 17 in Scheme 4, and is subjected to malonic ester synthesis and akylation with isopropyl iodide to give the malonic ester derivative 20. Protection on the hydroxyl function is changed from Thp to Bzl to yield 21 and the latter is subjected to protonolysis and decarboxylation. In the resulting isostere acid 22 amino protection is changed from Pht to Boc yielding the protected isostere 23 suitable for incorporation into polypeptide analogues, see Example XIV herein.

Keto isosteres may be prepared for example by the method of published U.K. Specification No. 1 587 809 (U.S. Pat. No. 4,242,256) of R. Sharpe and one of the present inventors M. Szelke, to which reference may be made. Alternatively they may be prepared from hydroxy isosteres prepared as disclosed herein and in particular, in the present Example, from the final product 23 of scheme 5 as in the scheme below (scheme 6):

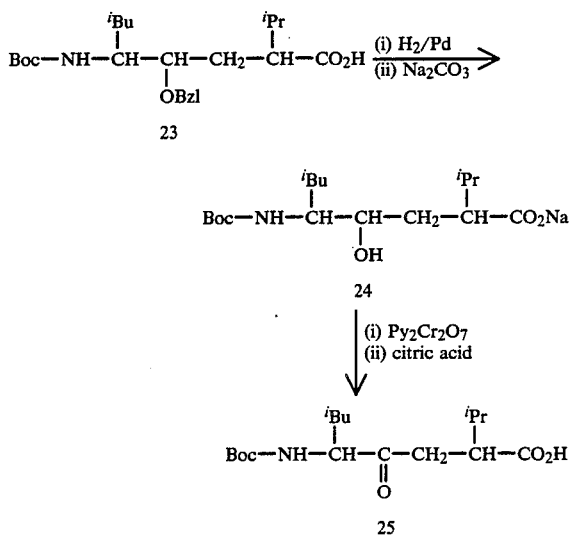

In the above scheme the benzyl protection is selectively removed from the hydroxyl function of 23 and the free acid is converted into its sodium salt 24. The latter is subjected to oxidation by pyridinium dichromate and acidification to give the partially protected keto isostere acid 25 suitable for incorporation into polypeptide analogues, see Example XV herein.

Alternatively the keto isostere may be prepared directly by a modified version of scheme 5 wherein the bromohydrin 19 is replaced by the bromoketone 15 of scheme 4 as follows (scheme 7):

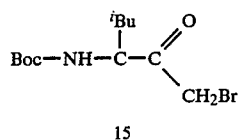

reacted with sodium isopropyl bis (trichloroethyl) malonate to give:

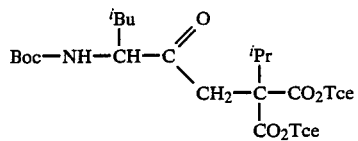

which is (1) treated with zinc/acetic acid and (2) reflexed in toluene to give:

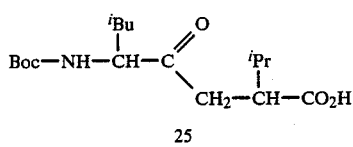

As an alternative to the above scheme 5 the following is preferred (scheme 8):

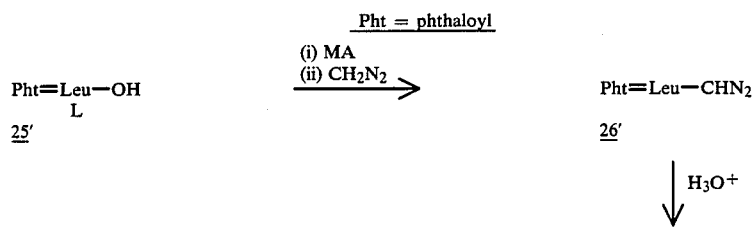

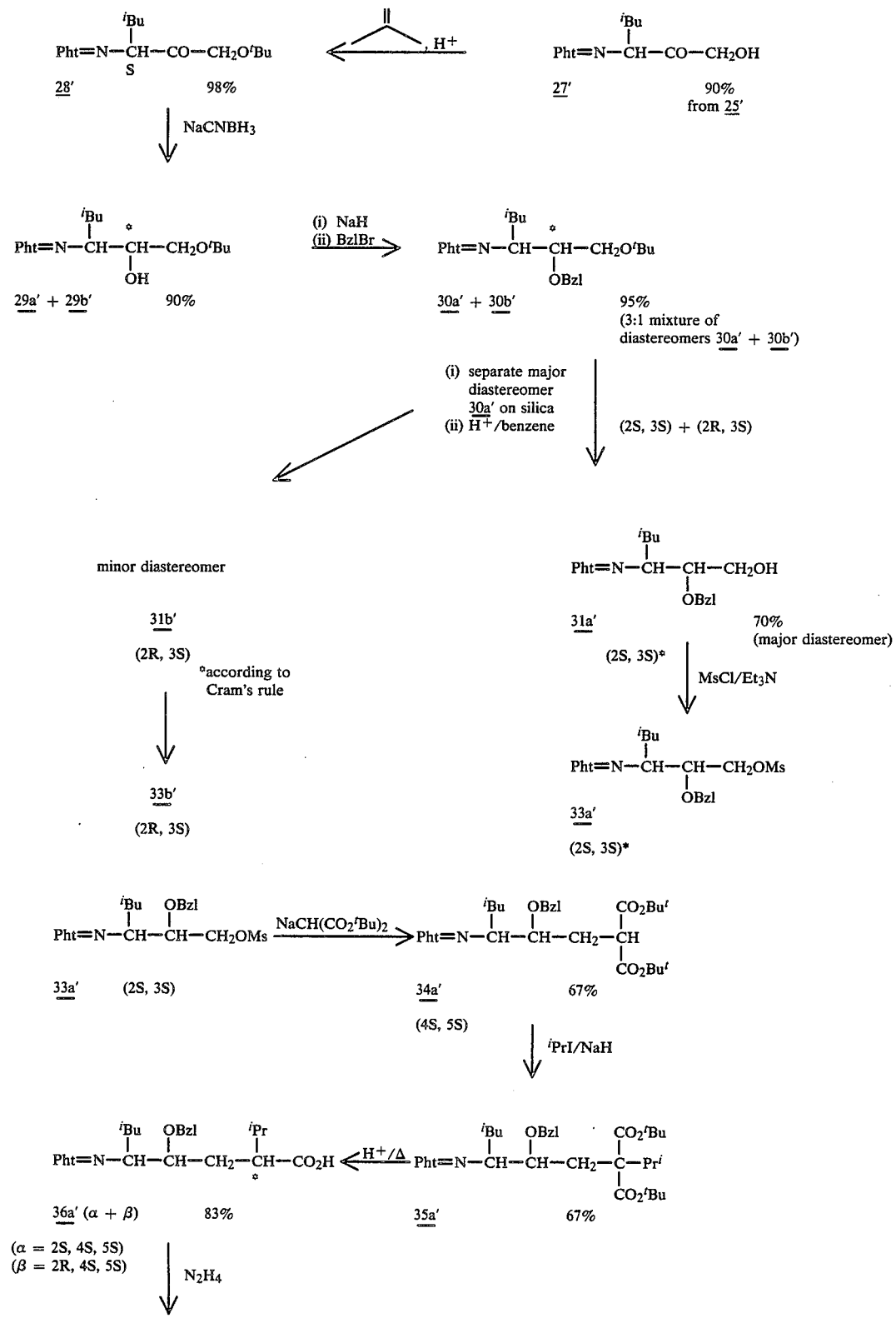

-continued
Pht = phthaloyl

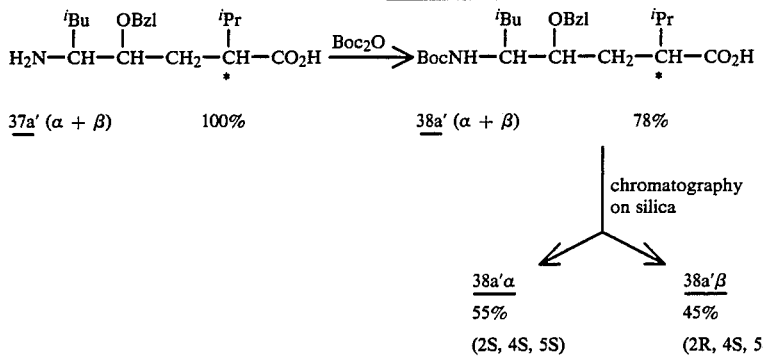

38a'α 55% (2S, 4S, 5S)

38a'β 45% (2R, 4S, 5S)

These dipeptide analogues are suitable for incorporation in polypeptide analogues.

PART B

The following are detailed examples.

ILLUSTRATION OF PREPARATION OF COUPLED RESIN

The Examples are preceded by the preparation of Boc-Tyr[Bzl(2,6Cl₂)]-O-resin. (Reaction times marked * are convenient rather than necessary.)

Preparation of Resin

Boc-Tyr[Bzl(2,6Cl₂)]-OH (1.65 g, 3.75 mmol) was dissolved in ethanol (20 ml) and water (5 ml) added. The pH was brought to 7.0 with cesium bicarbonate solution and the solvent evaporated in vacuo. The residue was treated twice with toluene and evaporated to remove the last traces of water leaving a white powder which was dried for several hours over phosphorus pentoxide. The residue was dissolved in DMF (65 ml), chloromethylated resin (10 g, 7.5 mequiv.) added and the reaction stirred at 37° for four days.

The resin was then filtered and washed thoroughly with DMF, DMF/water (9:1) and then DMF again. The resin was then resuspended in DMF (65 ml) and treated with acetic anhydride (2.36 ml, 25 mmol) and triethylamine (3.5 ml, 25 mmol) for 3 days.

The resin was filtered, washed thoroughly with DMF, DMF/water (9:1) and methanol and dried. The resin was then "defined" by shaking a suspension in dichloromethane and removing the particles slowest to float. The resin was then dried.

Yield 10.8 g.

Amino-acid analysis: (12N-HCl/propionic acid 1:1 130°, 2 hours gave an incorporation of 0.11 mmol/g.

EXAMPLES OF PARTICULAR ANALOGUES

EXAMPLE I

H-His-Pro-Phe-His-Leu-reduced-Leu-Val-Tyr-OH (H-76)

Boc-Tyr[Bzl(2,6Cl₂)]-O-Resin (3 g, 0.6 mmol) was washed with reagents in the following sequence: CH₂Cl₂ (3×) iPrOH (2×), CH₂Cl₂ (3×), 40% TFA/CH₂Cl₂ 1 min then 20 min, CH₂Cl₂ (3×), iprOH (2×), CH₂Cl₂ (3×), 40% TFA/CH₂Cl₂ 1 min then 20 min, CH₂Cl₂ (3×) iPrOH (2×) CH₂Cl₂ (3×), 10% Et₃N/CH₂Cl₂ (2×2 min), CH₂Cl₂ (5×). Boc-Val-OH (0.65 g, 3 mmol) was then coupled using DCCI (0.68 g, 3.3 mmol) and HOBt (0.92 g, 6 mmol) in DMF/CH₂Cl₂ (1:1) for 17 hours. The resin was then washed with DMF (3×), CH₂Cl₂(3×), iPrOH (2×), CH₂Cl₂ (3×) 10%, Et₃N/CH₂Cl₂ (2 min), CH₂Cl₂ (5×) then acetylated using acetylimidazole (0.66 g, 6 mmol) in DMF for 1 hour. The resin was then washed with DMF (3×) CH₂Cl₂ (3×) iPrOH (2×) and finally CH₂Cl₂ (3×). This sequence of washes and reactions was repeated for the addition of each of the residues with the following modifications.

After deprotection of the Boc-Val-Tyr[Bzl(2,6Cl₂]-O-resin Boc-NH-CH (CH₂CHMe₂)-CH₂-N(SO₂Ph)-CH(CH₂CHMe₂)-CO₂H (0.42 g, 0.9 mmol) was coupled using DCCI (0.28 g, 1.35 mmol) and HOBt (0.275 g, 1.8 mmol) in DMF/CH₂Cl₂ (1:1) for 18 hours, followed by acetylation using acetylimidazole (0.66 g, 6 mmol) in DMF for 1 hour.

After deprotection, Boc-His(Dnp)-OH (1.44 g, 3 mmol) was coupled using DCCI (0.68 g, 3.3 mmol) and HOBt (0.92 g, 6 mmol) for 2 hours, followed by acetylation for 1 hour.

Deprotection of the histidyl peptide was achieved using 50% TFA/CH₂Cl₂ instead of the usual 40% TFA/CH₂Cl₂. Boc-Phe-OH (0.796 g, 3 mmol) was coupled using DCCI (0.68 g, 3.3 mmol) and HOBt (0.92 g, 6 mmol) for 17½ hours, followed by acetylation for 1 hour.

Deprotection of the phenylalanyl peptide was achieved using the usual 40% TFA/CH₂Cl₂. Boc-Pro-OH (0.646 g, 3 mmol) was coupled using DCCI (0.68 g, 3.3 mmol) and HOBt (0.92, 6 mmol) for 2 hours followed by acetylation for 1 hour.

After deprotection Boc-His(Dnp)-OH (1.44 g, 3 mmol) was coupled using DCCI (0.68 g, 3.3 mmol) and HOBt (0.92 g, 6 mmol) for 14½ hours followed by acetylation for 1 hour.

The resin was then washed with DMF (3×), CH₂Cl₂(3×) iPrOH (2×), CH₂Cl₂(3×) and finally MeOH (3×) and dried to give 3.5353 g of product.

1.2 g of this material was treated with HF at 0° for 1¼ hours in the presence of anisol (1.5 ml) then dried overnight over potassium hydroxide. The resin was then washed with DMF/water (1:1), acetic acid and finally acetic acid/water (1:1) to remove the peptide. These washes were combined and evaporated in vacuo.

The residue was dissolved in DMF (15 ml) and water (6 ml) thioethanol (5 ml) added and the pH of the solution brought to 8.0 with sodium carbonate. The reaction was stirred overnight the solvent evaporated and the residue applied to a Sephadex G 25 column (72×2.5 cms) eluted with 50% acetic acid at 18 mls/hr collecting 6 ml fractions. Fractions 27-46 were combined and the solvent evaporated in vacuo and dried. Then 90% of the residue was taken (for the rest see Example III) and dissolved in anhydrous ammonia (100 ml) and small portions of sodium wire added until a permanent blue colour was achieved for 15 seconds. The ammonia was allowed to evaporate and the residue dried.

The residue was applied to a Sephadex SPC25 column (77×1.6 cms) eluted with 30% acetic acid at 40 mls/hr, with a sodium chloride gradient from 0.01M to 1M over two days collecting 6.6 ml fractions.

The product was contained in fractions 100–104. These were pooled, evaporated and the residue dissolved in glacial acetic acid and filtered to remove the sodium chloride. The solution was evaporated and desalted on a Sephadex G25 column (72×2.5 cms) eluted with 50% acetic acid at 18 mls/hr collecting 6 ml fractions. Fractions 32–6 were pooled, evaporated, transferred to a vial and lyophilised.

Yield 13.4 mg.
Product $C_{52}H_{74}O_9N_{12}$.
MW. 1011,25.
T.l.c. (silica) Rf 0.15 EtOAc/Pyr/AcOH/H$_2$O 40:20:6:11. Rf 0.40 nBuOH/Pyr/AcOH/H$_2$O 30:20:6:24.
T.l.e. pH 2.1 1000 V 30 min mobility 8.3 cm. pH 6.5 1000 V 30 min mobility 7.5 cm.
AAA 6N HCl+phenol 110°, 40 hours, peptide content 72%.
His: 1.97; Pro: 1.01; Val: 1.02; Tyr: 0.98; Phe: 1.01.

Example II

H-Pro-Phe-His-Leu-reduced-Leu-Val-Tyr-OH (H-79)

Fractions 80–84 of the SPC 25 Sephadex column from the previous synthesis were combined, evaporated and the residue dissolved in glacial acetic acid and filtered to remove sodium chloride. The solution was evaporated and the product desalted on a Sephadex G25 column (72×2.5 cms) eluted with 50% acetic acid at 18 mls/hr collecting 6 ml fractions. Fractions 32–9 were pooled, evaporated, transferred to a vial and lyophilised.

Yield 23.6 mg.
Product $C_{46}H_{67}O_8N_9$.
MW 874,10.
Tlc (silica) Rf 0.29 EtOAc/Pyr/AcOH/H$_2$O 40:20:6:11. Rf 0.46 nBuOH/Pyr/AcOH/H$_2$O 30:20:6:24.
Tle pH 2.1 1000 V 30 min mobility 7.5 cms. pH 6.5 1000 V 30 min mobility 8.3 cms.
AAA 6N HCl+phenol, 110°, 40 hours, peptide content 85%.
His: 0.97; Pro: 1.08; Val: 0.99; Tyr: 0.97; Phe: 1.00.

The above example illustrates how Y in formulae (V), (VA) and (VB) may be absent.

Example III

H-His-Pro-Phe-His-Leu-reduced (SO$_2$Ph)-Leu-Val-Tyr-OH (H-78)

In the synthesis of compound H76 10% of the residue from the Sephadex G25 column after the HF and thioethanol treatments of the resin was kept.

This material was applied to a Sephadex SPC25 column (77×1.6 cm) eluted with 30% acetic acid at 20 mls/hr with a sodium chloride gradient from 0.01M to 1M over 2 days collecting 6.6 ml fractions.

The product was contained in fractions 74–7. These were pooled, evaporated, dissolved in glacial acetic acid and filtered to remove sodium chloride. The solution was then evaporated and desalted on a Sephadex G25 column (72×2.5 cms) eluted with 50% acetic acid at 18 mls/hr collecting 6 ml fractions. Fractions 31–4 were pooled evaporated, the residue transferred to a vial and lyophilised.

Yield 0.6 mg.
Product $C_{58}H_{78}O_{11}N_{12}S$.
MW: 1151.40.
Tlc (silica) Rf 0.31 EtOAc/Pyr/AcOH/H$_2$O 40:20:6:11.
Tle pH 2.1 1000 v 30 min mobility 5.4 cms.
AAA 6N HCl+phenol, 40 hrs, 110°, peptide content 64%. His: 1.93; Pro: 1.08; Val: 1.05; Tyr: 0.96; Phe: 0.97.

Example IV

H-DHis-Pro-Phe-His-Leu-reduced-Leu-Val-Tyr-OH, (H-77)

The Boc-Tyr [Bzl(2,6,Cl$_2$)]-O-Resin (3 g, 0.6 mmol) was deprotected and Boc-Val-OH (0.65 g, 3.0 mmol) was coupled using DCCI (0.68 g, 3.3 mmol) and HOBt (0.92 g, 6 mmol) for 22 hours* then acetylated with acetylimidazole (0.66 g, 6 mmol) for 1 hour.

After deprotection, Boc-Leu-reduced (SO$_2$Ph)-Leu-OH, IV, (0.4 g, 0.9 mmol) was coupled using DCCI (0.28 g, 1.35 mmol) and HOBt (0.275 g, 1.8 mmol) for 20 hours, then acetylated for 1 hour.

After deprotection Boc-His(Dnp)-OH (1.44 g, 3 mmol) was coupled using DCCI (0.68 g, 3.3 mmol) and HOBt (0.92 g, 6 mmol) for 22 hours, then acetylated for 1 hour.

After deprotection, this time with 50% TFA/CH$_2$Cl$_2$ Boc-Phe-OH (0.796 g, 3 mmol) was coupled with DCCI (0.68 g, 3.3 mmol) and HOBt (0.92 g, 6 mmol) for 19 hours* then acetylated for 1 hour.

After deprotection Boc-Pro-OH (0.646 g, 3 mmol) was coupled using DCCI (0.68 g, 3.3 mmol) and HOBt (0.92 g, 6 mmol) for 3 hours then acetylated for 1 hour.

The peptide was again deprotected and coupled with Boc-D-His(Boc)-OH (0.91 g, 2.56 mmol using DCCI (0.58 g, 2.82 mmol) and HOBt (0.78 g, 5.1 mmol) for 2 hours, then acetylated for 1 hour.

The resin was washed with DMF (3×) CH$_2$Cl$_2$ (3×) iProH (2×) CH$_2$Cl$_2$ (3×) and finally MeOH (3×) and dried to give 3.6563 g of product.

1.2 g of this material was treated with HF at 0° for 1¼ hours in the presence of anisole (1.5 ml) then dried overnight over potassium hydroxide. The resin was then washed with DMF, DMF/H$_2$O (1:1), acetic acid and finally acetic acid/water (1:1) to remove the peptide. These washes were combined and evaporated in vacuo.

The residue was dissolved in DMF (15 ml) and water (6 ml) thioethanol (5 ml) added and the pH of the solution brought to 8.0 with sodium carbonate solution. The reaction was stirred overnight, the solvent evaporated and the residue applied to a Sephadex G 25 column (72×2.5 cms) eluted with 50% acetic acid at 18 mls/hr collecting 6 ml fractions. Fractions 27–46 were combined and the solvent evaporated in vacuo and dried.

90% of the residue was dissolved in anhydrous ammonia (100 ml) and small portions of sodium wire added until a permanent blue colour was achieved for 15 seconds. The ammonia was allowed to evaporate and the residue dried.

The residue was applied to a Sephadex SPC 25 column (77×1.6 cms) eluted with 30% acetic acid at 20 mls/hr with a sodium chloride gradient 0.01M to 1M over 2 days collecting 6.6 ml fractions.

The product was contained in fractions 88–92. These were pooled, evaporated and the residue dissolved in glacial acetic acid and filtered to remove the sodium chloride. The solution was evaporated and desalted on a Sephadex G 25 column (72×2.5 cms) eluted with 50% acetic acid at 18 mls/hr collecting 6 ml fractions. Fractions 32–41 were pooled, evaporated, transferred to a vial and lyophilised.

Yield 46.8 mg.

Difference in yields between "L-His" and "D-His" compounds was accounted for by a lower incorporation of the isostere in the "L" case and less removal of the histidine with Na/NH$_3$.

Product $C_{52}H_{74}O_9N_{12}$.

MW 1011,25.

Tlc (silica Rf 0.18 EtOAc/Pyr/AcOH/H$_2$O 40:20:6:11.

Tle pH 2.1 1000 V 30 min mobility 7.7 cm. pH 6.5 1000 V 30 min mobility 7.9 cm.

AAA 6N-HCl+phenol, 110°, 40 hours, peptide content 93%.

His: 1.98; Pro: 1.00; Val: 1.08; Tyr: 0.97; Phe 0.97.

Example V

H-His-Pro-Phe-His-Leu-reduced-Val-Ile-His-OH (H 113)

The method is generally that of Example I above but illustrates formula (VB).

Preparation of Boc-His (DNP)-O-Resin (AH/30/83)

Boc-His(DNP)-OH. (4.74 g, 11.25 mmol) was dissolved in ethanol (60 ml) and a solution of cesium bicarbonate (2.18 g, 11.25 mmol) in water (15 ml) added. The solvent was evaporated in vacuo and the residue treated four times with toluene and evaporated to remove water before finally drying overnight over phosphorus pentoxide. The residue was dissolved in DMF (175 ml), chloromethylated resin (30 g, 22.5 m-equiv.) added and the reaction stirred at 37° for five days.

The resin was filtered off and washed thoroughly with DMF, DMF/water (9:1) and then DMF again. It was resuspended in DMF (175 ml) and treated with acetic anhydride (7.08 ml, 75 mmol) and triethylamine (10.5 ml, 75 mmol) overnight.

The resin ester was filtered, washed thoroughly with DMF, DMF/water (9:1) and methanol and dried. It was then "de-fined" by shaking it in dichloromethane and removing the particles in the supernatant. Finally, the resin was dried. Yield: 30.45 g. A trial coupling with Boc-Ala-OH, followed by amino-acid analysis (after hydrolysis with 12N-HCl/propionic acid 1:1, 130°, 2 hrs) gave an incorporation of 0.22 mmol/.

Coupling to Resin Ester

Boc-His(DNP)-O-Resin (2.5 g 0.55 mmol) was deprotected with 50% TFA/CH$_2$Cl$_2$ and Boc-Ile-OH (0.748 g 3 mmol) was coupled using DCCI (0.68 g, 3.3 mmol) and HOBt (0.92 g, 6.0 mmol) for 2 hours, then acetylated with acetyl imidazole (0.55 g, 5 mmol) overnight.

After deprotection with 40% TFA/CH$_2$Cl$_2$, Boc-Leu-reduced (3,4-Cl$_2$-Z)-Val-OH, 4 (0.343 g, 0.66 mmol) was coupled using DCCI (0.15 g, 0.73 mmol) and HOBt (0.202 g, 1.32 mmol) for 16 hours, then acetylated for 1 hour.

After deprotection, Boc-His(DNP)-OH (1.26 g, 3.0 mmol) was coupled using DCCI (0.68 g, 3.3 mmol) and HOBt (0.92 g, 6 mmol) for 2 hours, then acetylated for 1 hour.

After deprotection again with 50% TFA/CH$_2$Cl$_2$, Boc-Phe-OH (0.796 g, 3 mmol) was coupled with DCCI (0.68 g, 3.3 mmol) and HOBt (0.92 g, 6 mmol) for 3 hours, then acetylated overnight*

After deprotection, Boc-Pro-OH (0.646 g, 3 mmol) was coupled using DCCI (0.68 g, 3.3 mmol) and HOBt (0.92 g, 6 mmol) for 2 hours then acetylated for 1 hour.

The peptide was again deprotected and coupled with Boc-His (DNP)-OH (1.26 g, 3 mmol) using DCCI (0.68 g, 3.3 mmol) and HOBt (0.92 g, 6 mmol) for 2 hours, then acetylated overnight.

The peptide resin ester was washed with DMF (3×), CH$_2$Cl$_2$ (3×) iProH (2×), CH$_2$Cl$_2$ (3×) and finally MeOH (3×) and dried. It was then treated with HF at 0° for 1¼ hours in the presence of anisole (4 ml) and dried overnight over potassium hydroxide. The resin was washed with DMF, acetic acid and acetic acid/water (1:1) to remove the peptide. The washes were combined and evaporated in vacuo.

The residue was dissolved in DMF (60 ml) and water (24 ml), thioethanol (10 ml) was added and the pH of the solution brought to 8.0 with sodium carbonate solution. The reaction mixture was stirred overnight, the solvent evaporated and the residue applied to a Sephadex G25 column (77×2.5 cms). It was eluted with 50% acetic acid at 18 mls/hr collecting 6 ml fractions. Fractions 34–53 were combined and the solvent evaporated in vacuo and dried.

Product $C_{49}H_{72}O_3N_{14}$.

MW 985,21.

Tlc (silica) Rf=0.63 in EtOAc-Py-AcOH-H$_2$O (15:20:6:11).

AA analysis in accordance with calculated composition.

Examples VI–IX

These examples illustrate formula (VA). The methods described herein are applied to condensing Boc-Phe-H or Boc-Leu-H with H-Phe-OBzl, reducing the imine link, deprotecting at the carboxyl terminus and protecting the nitrogen of the reduced peptide link to give:

$$\text{Boc—NH—CH(R)—CH}_2\text{—N(ZCl}_2\text{)—CH(Bzl)—CO}_2\text{H}$$

12 R=Bzl
12a R=iBu
ZCl$_2$=3,4-dichloro benzyloxy carbonyl

This Phe-reduced-Phe or Leu-reduced-Phe analogue is then used as follows:

VI Use of 12 (Phe-reduced-Phe) in an analogue otherwise as H-77 (see Example IV)

VII Use of 12a (Leu-reduced-Phe) in an analogue otherwise as H-77 (see Example IV)

VIII Use of 12 in an analogue as H-76 (Example I), viz:

(H 110)

H—His—Pro—Phe—His—Phe—reduced-Phe—Val—Tyr—OH
  6    7    8    9   10      11       12   13

IX Use of 12a in an analogue as H-76 (Example I), viz:

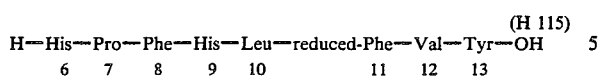
(H 115)

Example X

This example illustrates formula (VB), the method of Example V being used but with the Tyr resin of Examples I to IV, to give:

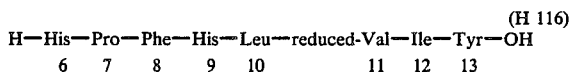
(H 116)

Example XI

Use of the methods disclosed herein to give:

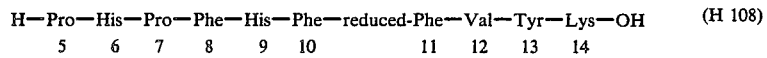
(H 108)

this being an analogue illustrating the non-criticality of the terminal portions of the chain allowing X and W in formulae (V), (VA) and (VB) to represent further residues. It is a further example of formula (VA).

Example XII

Use of the methods disclosed herein to give:

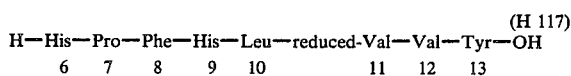
(H 117)

a compound of value in its relation to the Leu-Val structure at 11, 12 in human renin substrate.

The following example illustrates the synthesis of hydroxy and keto isosteres.

Example XIII

Taking the product of scheme 4 earlier herein, giving an N-terminal phthaloyl protected, -OH protected hydroxy isostere of Leu-Leu can be coupled direct for example to valyl tyrosine, followed by removal of the phthaloyl group, coupling direct to a suitable tri or tetrapeptide, and deprotection at the -OH group by mild acid hydrolysis, to give for example analogues corresponding to H-76 (Example 1), H-79 (Example 2), H-77 (Example 4). Alternatively the phthaloyl group may be removed by treatment with hydrazine and a new protective group, e.g. benzyloxycarbonyl or t-butyloxycarbonyl attached prior to coupling. The methods used after the preparation of the protected hydroxy isostere are those of the peptide synthesis art, well known in themselves and exemplified in detail herein. The compounds specifically prepared are:
(a) H-His-Pro-Phe-His-Leu-hydroxy-Leu-Val-Tyr-OH
(b) H-Pro-Phe-His-Leu-hydroxy-Leu-Val-Tyr-OH
(c) H-DHis-Pro-Phe-His-Leu-hydroxy-Leu-Val-Tyr-OH

Example XIV

The compound 23 (scheme 5 herein) is incorporated into an octapeptide analogue by the usual methods of solid phase peptide synthesis to give:

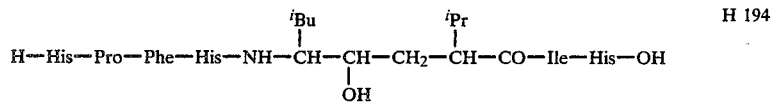
H 194

This is a Leu-hydroxy-Val isostere, and the full synthesis may be as set out in scheme 9 below:

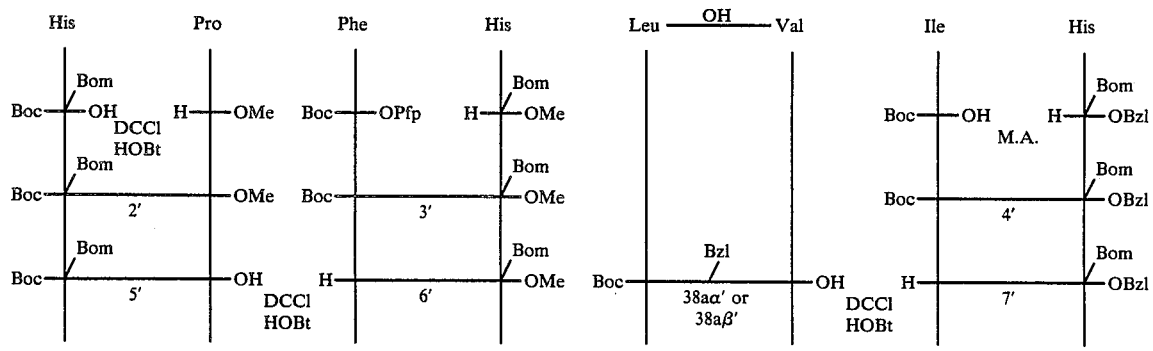

-continued
Scheme 9

[Scheme 9 diagram]

14a (from 38aα') = H-195
14b (from 38aβ') = H-194
Structure
H—His Pro Phe His Leu—OH—Val Ile His—OH
(H 194, H 195)
Compound 13a' above is H 261

Example XV

The compound 25 (scheme 6 herein) is incorporated into an octapeptide analogue by the usual methods of solid phase synthesis, the analogue being:

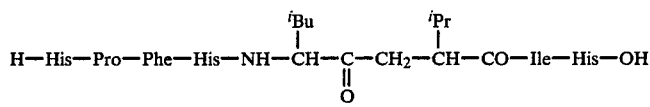

This is a Leu-keto-Val isostere.

Examples XVI–XL

The table following Table 1, shows the structures and the activity, of further examples of compounds made by following the methods set out in detail for corresponding sequences in the preceding examples. For example for H 184, H 185, starting from the methyl ester of Boc-L-leucine a protected Leu-reduced-Val isostere is made by the synthetic route set out in scheme 3 herein. It is converted to Leu-reduced-Val Ile His D-Lys-OH, His Leu-reduced-Val Ile His D-Lys-OH and Phe His Leu-reduced-Val Ile His D-Lys-OH by standard methods of peptide synthesis, as illustrated herein. Compounds H 157 and H 184 to H 188 in these examples of compounds represent partial sequences of formula V, as also shown in Example II. The activity of H 157 may be noted; H 184 to H 186 show lower but still potentially interesting activities.

TABLE I

| Ex. | | 5 | 6 | 7 | 8 | 9 | 10 | 11 | 12 | 13 | 14 | IC$_{50}$, μM human |
|---|---|---|---|---|---|---|---|---|---|---|---|---|
| XVI | .I-135 | | H—His | Pro | Phe | His | Leu $\underline{R}$ Val | | Ile | DTyr—OH | | 1.0 |
| XVII | 140 | H—Pro | His | Pro | Phe | His | Leu $\underline{R}$ Val | | | His—NH(CH$_2$)$_3$NH$_2$ | | 4.5 |
| XVIII | 141 | H—Pro | His | Pro | Phe | His | Leu $\underline{R}$ Val | | | His—NH(CH$_2$)$_5$NH$_2$ | | 3.0 |
| XIX | 142 | H—Pro | His | Pro | Phe | His | Leu $\underline{R}$ Val | | Ile | His | Lys—OH | 0.008 |
| XX | 145 | H—Pro | His | Pro | Phe | His | Leu $\underline{R}$ Val | | Ile | Tyr—NH(CH$_2$)$_5$NH$_2$ | | 3 |
| XXI | 147 | | H—His | Pro | Phe | His | Leu $\underline{R}$ Val | | Ile | His | DLys—OH | 0.05 |
| XXII | 148 | H—Pro | His | Pro | Phe | His | Leu $\underline{R}$ Val | | Ile | His—OH | | 0.01 |
| XXIII | 149 | H—DPro | His | Pro | Phe | His | Leu $\underline{R}$ Val | | Ile | His—OH | | 0.025 |
| XXIV | 152 | | H—Arg | Pro | Phe | His | Leu $\underline{R}$ Val | | Ile | Tyr—OH | | 0.55 |
| XXV | 153 | | H—His | Pro | Phe | His | Leu $\underline{R}$ Val | | Ile | Tyr | Lys—OH | 0.036 |
| XXVI | 154 | | H—His | Pro | Phe | His | Leu $\underline{R}$ Val | | Ile | Tyr | Lys—OH | 0.17 |

TABLE I-continued

| Ex. | | 5 | 6 | 7 | 8 | 9 | 10 11 | 12 | 13 | 14 | IC$_{50}$, μM human | baboon |
|---|---|---|---|---|---|---|---|---|---|---|---|---|
| XXVII | 155 | H—Pro | His | Pro | Phe | His | Leu $\underline{R}$ Val | Ile | Tyr | Lys—OH | 0.016 | |
| XXVIII | 156 | H—Pro | His | Pro | Phe | His | Leu $\underline{R}$ Val | Ile | Tyr | Lys—OH | 0.040 | |
| XXIX | 157 | | | H—Pro | Phe | His | Leu $\underline{R}$ Val | Ile | His | DLys—OH | 0.025 | |
| XXX | 158 | H—Pro | His | Pro | Phe | His | Leu $\underline{R}$ Val | Ile | Tyr—OH | | 0.048 | |
| XXXI | 165 | | H—His | Pro | Phe | His | Leu $\underline{R}$ Val | Ile | His | Lys—OH | 0.06 | |
| XXXII | H-168 | | H—His | DPro | Phe | His | Leu $\underline{R}$ Val | Ile | His—OH | | 5.5 | |
| XXXIII | 184 | | | | | | H—Leu $\underline{R}$ Val | Ile | His | DLys—OH | | |
| XXXIV | 185 | | | | | H—His | Leu $\underline{R}$ Val | Ile | His | DLys—OH | | |
| XXXV | 186 | | | | H—Phe | His | Leu $\underline{R}$ Val | Ile | His | DLys—OH | | |
| XXXVI | 187 | | | H—Pro | Phe | His | Leu $\underline{R}$ Val | Ile | His | DLys—OH | 2.6 | |
| XXXVII | 188 | | | Ac—Pro | Phe | His | Leu $\underline{R}$ Val | Ile | His | DLys—OH | 0.6 | |
| XXXVIII | 190 | H—Pro | His | Pro | Phe | His | Leu $\underline{R}$ Val | Ile | His | DLys—OH | 0.1 | 0.05 |
| XXXIX | 191 | | H—DHis | Pro | Phe | His | Leu $\underline{R}$ Val | Ile | His | DLys—OH | 0.2 | 0.15 |
| XL | 192 | H—Pro | DHis | Pro | Phe | His | Leu $\underline{R}$ Val | Ile | His | DLys—OH | 0.2 | 0.2 |

PART C

Further Examples

Table 2 below is of examples of compounds with the modified 10,11 isosteric links disclosed above applied to hexapeptide or smaller analogues.

TABLE 2

| Ex. | Code | X | 8 | 9 | 10 11 | 12 | 13 | W | IC$_{50}$μM v/s human renin |
|---|---|---|---|---|---|---|---|---|---|
| XLI | H262 | H— | | | Leu $\underline{OH}$ Val | Ile | His | Lys—OH | 11 |
| XLII | H265 | Boc— | | | Leu $\underline{OH}$ Val | Ile | His—OH | | |
| XLIII | H266 | H— | | | Leu $\underline{OH}$ Val | Ile | His—OH | | 29 |
| XLIV | H267 | Boc— | | His | Leu $\underline{OH}$ Val | Ile | His—OH | | |
| XLV | H268 | H— | | His | Leu $\underline{OH}$ Val | ILe | His—OH | | |
| XLVI | H269 | Boc—Phe | | His | Leu $\underline{OH}$ Val | Ile | His—OH | | 0.007 |
| XLVII | H270 | H—Phe | | His | Leu $\underline{OH}$ Val | Ile | His—OH | | 5 |
| XLVIII | H282 | Boc—Phe | | His | Leu $\underline{OH}$ Gly | Ile | His—OH | | 0.3 |
| XLIX | H286 | Boc—Phe | | His | Leu $\underline{OH}$ Val | Ile | Phe—OMe | | 0.018 |
| L | H287 | Boc—Phe | | His | Leu $\underline{OH}$ Val | Ile | —OMe | | 0.005 |
| LI | H288 | Boc—Phe | | His | Leu $\underline{OH}$ Val | Ile | His—OMe | | 0.0035 |
| LII | H289 | Boc—Phe | | His | Leu $\underline{K}$ Val | Ile | His—OH | | |

TABLE 2-continued

| Ex. | Code | X | 8 | 9 | 10 | 11 | 12 | 13 | W | IC$_{50}\mu M$ v/s human renin |
|---|---|---|---|---|---|---|---|---|---|---|
| LIII | H290 | Boc—Phe | Ala | | Leu$\xrightarrow{OH}$Val | | Ile | His—OH | | |
| LIV | H291 | Boc—Phe | Phe | | Leu$\xrightarrow{OH}$Val | | Ile | His—OH | | |
| LV | H294 | Boc—Phe | His | | Leu$\xrightarrow{R}$Val | | Ile | His—OH | | |

The synthesis of the reduced, keto, and hydroxy analogues in the above table is generally by the methods given earlier herein, the dipeptide analogues being prepared first and incorporated in the full sequence by essentially standard methods of peptide synthesis. In particular hydroxy or keto isosteres of dipeptides may be made by the method given earlier wherein a derivative of a halohydrin, preferably a bromohydrin, or haloketone, preferably a bromoketone, gives the desired isostere as such or in protected form.

A further, preferred, synthesis of hydroxy and hence keto dipeptide isosteres is given below, applied to Leu-hydroxy-Val and referring to scheme 10 following, which is a later version of scheme 8 herein.

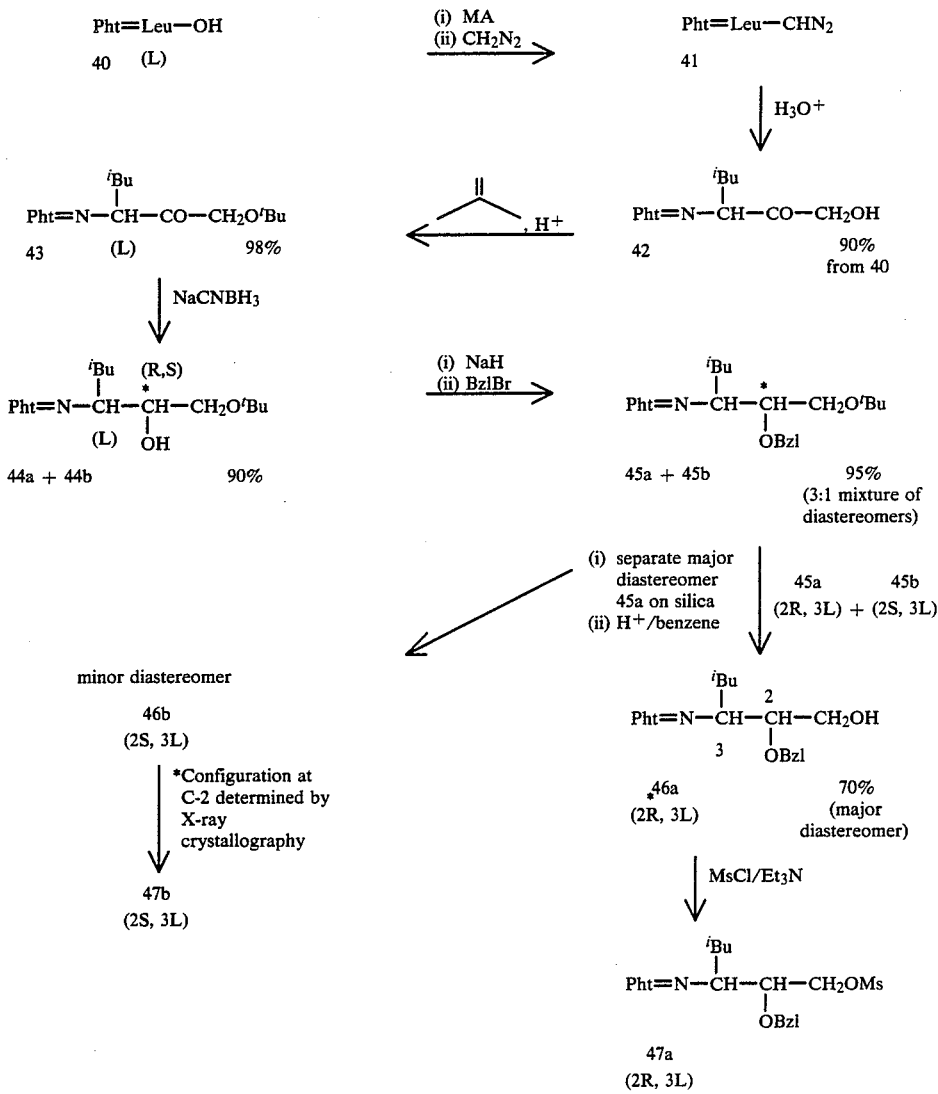

Scheme 10

-continued
Scheme 10

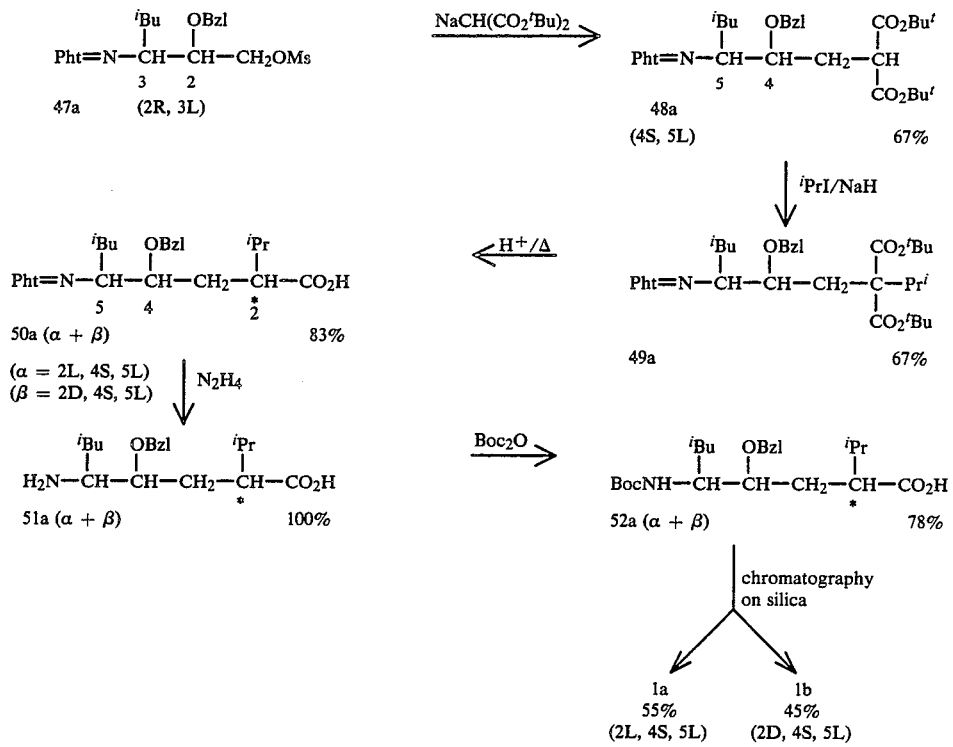

Synthesis of Protected Leu-OH-Val 1a (1) Phthalimido-ketol 42

(a) A solution of phthaloyl-L-leucine (60 mmol) in ethyl acetate (150 ml) was cooled to −10° C., N-methyl-morpholine (60 mmol) was added followed by Isobutyl chloroformate (60 mmol) at such a rate that the temperature never exceeded −10° C. After 10 mins. at −10° C., the N-methyl-morpholine hydrochloride was filtered off and the solution of mixed anhydride poured into a solution of diazomethane (approx. 130 mmol, dried over KOH pellets) in ether (500 ml). After 3 hours at 22° C., the solvent was evaporated and the crude diazoketone 41 was obtained as an orange oil. IR Spectrum (film) νmax 2100 cm$^{-1}$.

(b) The above diazoketone was dissolved in dioxan (200 ml), 1M $H_2SO_4$ (100 ml) added and the mixture was heated at 75° for 30 mins. The reaction mixture was cooled, its pH adjusted by the slow addition of NaHCO$_3$ to 5 and the dioxan was evaporated. The remaining aqueous solution was extracted with ethyl acetate, the extracts were washed with water and brine, dried over $Na_2SO_4$ and evaporated. The crude ketol 42 was crystallised from ether-petrol to give pale yellow platelets. In a subsequent preparation of crude ketol was found to be satisfactory by TLC (in petrol (60°-80°) containing 30% ethyl acetate) and was used without crystallisation.

(2) tert-Butyl ether 43

The ketol 42 from (1) (b) (50 mmol) was dissolved in dichloromethane (50 ml), cooled to −78° C. and liquid iso-butene (50 ml) and concentrated sulphuric acid (0.5 ml) were added. The reaction mixture was stoppered and kept at 22° C. for 72 hrs.

The reaction vessel was cooled and opened, and the pH of its contents was adjusted to 5 with NaHCO$_3$. The product was extracted with ether; ethereal extracts were washed with water, brine, dried over $Na_2SO_4$ and evaporated to yield the tert-butyl ether (98%).

(3) Diols 44a and 44b

A solution of the tert-butyl ether 43 (50 mmol) in tetrahydrofuran (150 ml) was cooled to 0° C. To it were added 1M HCl (25 ml) followed over a period of 20 mins. by NaCNBH$_3$ (250 mmol) in a mixture of tetrahydrofuran (100 ml) and water (20 ml). After stirring for 2 hrs. the pH of the solution was adjusted to 4, tetrahydrofuran was evaporated in vacuo, the residue was triturated with ether, the ethereal solution was washed with water and brine, dried and evaporated. A 3:1 mixture of the two diastereomers was obtained in 90% yield, the major component being the desired 2R,3L compound 44a. Progress of the reduction was monitored by TLC in chloroform.

(4) Benzyl ethers 45a and 45b (a) A mixture of the diastereomeric alcohols from (3) (40 mmol) was azeotroped three times with dry benzene and then dissolved in dry dimethyl formamide (100 ml). Under dry nitrogen, NaH (1 equivalent) was added with cooling in ice-water. After all NaH had reacted (approx. 10 mins.), benzyl bromide (1.5 equivalents) was added. The reaction mixture was stirred at 20° C. and the progress of benzylation was monitored by TLC in chloroform: petrol (60°-80°)=4:1 or in petrol (60°-80°) containing 10% ethyl acetate. It was complete after 2.5 hrs., when the reaction mixture was cooled, acidified with 1M citric acid and evaporated in vacuo. The residue was taken up in ether, washed with water and brine, dried and evaporated.

(b) Separation of the diastereomers 46a and 46b. The mixture from (a) was adsorbed onto silica, dried in vacuo and added to the top of a dry-packed column, which was eluted with petrol (60°-80°) containing 5% ethyl acetate. The major diastereomer 45a was eluted from the column first. Configuration at C-2 and C-3 was determined by X-ray crystallography and was found to be 2R, 3L for the major diastereomer 45a.

(5) Mesylate 47a (a) A solution of the major benzyl ether 45a (20 mmol) in dichloromethane (50 ml) was treated in an atmosphere of nitrogen with trifluoroacetic acid (50 ml). After 1.5 hrs. the reaction mixture was evaporated to dryness, and the residue taken up in ethyl acetate. The solution was carefully washed to neutrality with 1M NaHCO$_3$, water and brine, dried and evaporated to give the alcohol 46a. The latter can be crystallised from ethyl acetate-petrol (60°-80°) to furnish colorless needles, but chromatography on silica may be necessary to obtain a higher yield.

(b) A solution of the alcohol 46a from (a) (20 mmol) in dichloromethane (100 ml) was cooled to 0°, triethylamine (2 equivalents) and methane-sulphonyl chloride (1.1 equivalents) were added and the reaction mixture was stirred at 22° for 1 hr. It was evaporated, the residue dissolved in ethyl acetate, this solution washed with water and brine, dried and evaporated to leave an oil which crystallised on standing. The latter was recrystallised from dichloromethane-petrol (60°-80°) to give the mesylate 47a as glistening plates (90%).

(6) Malonic ester 48a

Di-tert-butyl malonate (24 mmol) was added to a slurry of sodium hydride (24 mmol) in 1,2-dimethoxyethane (120 ml) under dry nitrogen. After 10 mins., crystalline mesylate 47a (20 mmol) was added and the mixture was refluxed under nitrogen. Progress of the alkylation was monitored by TLC in chloroform-petrol (60°-80°) (7:3), the R$_F$ of the product being slightly higher than that of the mesylate. Reaction was complete after 24 hrs, when the mixture was cooled and poured into 1M citric acid solution. Solvents were evaporated in vacuo, the residue taken up in ethyl acetate, washed with water and brine, dried and evaporated to yield crude malonic ester 48a. The latter was purified by chromatography on a dry column of silica as described above for 45a in section (4) (b). Elution was carried out with chloroform-petrol (3:2) to give pure 48a in 67% yield as a colorless oil.

(7) iso-Propyl malonic ester 49a

Malonic ester 48a (15 mmol) was azeotroped three times with dry benzene, dissolved in dry tetrahydrofuran (50 ml) and added to a slurry of sodium hydride (1.1 equivalents) in tetrahydrofuran under dry nitrogen. After refluxing for 20 mins., isopropyl iodide (10 equivalents) was added and the mixture refluxed for a further hour. After cooling, 1M citric acid solution was added, the solvent evaporated and the residue taken up in ethyl acetate. After washing with water and brine and drying, ether was evaporated to leave the iso-propyl derivative 49a as a colorless oil (67%). Purity was checked by TLC in chloroform-petrol (7:3), and the product was either used directly in step (8) or, if necessary, first purified by chromatography on silica in chloroform-petrol (60°-80°) (3:2).

(8) Phthaloylamino carboxylic acids 50a $\alpha$ and $\beta$.

The di-tert-butyl ester 49a (15 mmol) was treated with 50% trifluroacetic acid in dichloromethane (100 ml) under nitrogen for 1.5 hrs. to remove the tert-butyl ester groups.

This mixture was evaporated to dryness, the residue dissolved in toluene and refluxed for 6 hrs. Decarboxylation was monitored by TLC in chloroform-methanol-acetic acid (62:4:1). On completion, the reaction mixture was evaporated to dryness, the last traces of solvent being removed by pumping in high vacuum. A mixture of the epimeric acids 50a$\alpha$ and 50a$\beta$ was obtained as an oil, and was either used directly in step (9) or, if necessary, purified by chromatography on silica using chloroform-methanol-acetic acid (97:2:1) for elution.

(9) Amino carboxylic acids 51a$\alpha$ and $\beta$

The phthaloyl derivatives 50a$\alpha$ and $\beta$ (10 mmol) were dissolved in ethanol (80 ml) and treated with hydrazine hydrate (10 equivalents) under reflux for 1.5 hrs. Removal of the phthaloyl group was monitored by TLC in chloroform-methanol-acetic acid (62:4:1). On completion, the reaction mixture was cooled, water was added to dissolve the precipitate formed, solvents were removed in vacuo and the residue was dried in vacuo over concentrated H$_2$SO$_4$ overnight. It was dissolved in the minimum amount of water, extracted with ether (10 ml), acetic acid was added to pH=4, the mixture cooled and the precipitated phthaloyl hydrazide was filtered off. Evaporation of the filtrate yielded a mixture of the amino acids 51a$\alpha$ and $\beta$.

(10) Boc-Amino acid 1a (a) Excess KHCO$_3$ was added to a solution of the amino acids 51a in water (20 ml), followed by di-tert-butyl dicarbonate (excess, depending on the amount of residual hydrazine present in 51a) dissolved in dioxan (20 ml). On completion of the reaction the pH was adjusted to 4, solvents were evaporated, the residue was dissolved in ethyl acetate and the solution was washed with water and brine.

After drying, the solvent was removed in vacuo, the residue triturated with petrol (60°-80°) and any N, N'-bis-Boc-hydrazine present removed by filtration. Evaporation of the petrol yielded crude Boc-acids 52a$\alpha$ and $\beta$. These were dissolved in ethyl acetate, N,N-dimethylaminoethylamine (approx. 2 g) was added to react with the excess di-tert-butyl dicarbonate present, and after 20 mins. the solution was extracted with 1M citric acid. It was washed with water, brine, dried and evaporated to give 52a$\alpha$ and $\beta$ as a pale yellow oil.

(b) The above mixture of epimeric acids was separated by chromatography on silica gel (40-60$\mu$, dry-packed column) eluting either with petrol containing 20% ethyl acetate (and possibly a small amount of acetic acid to prevent trailing), or with chloroform containing 2% methanol. Separation was monitored by TLC in chloroform-methanol-acetic acid (97:2:1). The more polar component was the required 2L, 4S, 5L epimer 1a.

H262 (Example XLI)

The Leu-OH-Val dipeptide isostere is prepared as given above and converted to Leu-OH-Val Ile His Lys-OH by, again, standard methods.

H265 and H266, H267 and H268, H269 and H270
(Examples XLII–XLVII)

These compounds, three pairs of respectively N-Boc protected and free N-terminal NH$_2$ isosteres, all with C-terminal Ile His-OH, are made starting with the protected Leu-OH-Val isostere prepared as given above. The synthesis is by methods in substance those of scheme 9 herein.

H282 (Example XLVIII)

This analogue contains Leu-OH-Gly, which is synthesised according to Scheme 10 except that the alkylation step with isopropyl iodide producing 49a from 48a is omitted, the synthesis proceeding on 48a. Otherwise the synthesis is as for H269.

H286, H287, H288 (Examples XLIX-LI)

These compounds, containing Leu-OH-Val isosteres, are made essentially as H269.

H289 (Example LII)

The Boc-Leu-keto-Val isostere made according to Scheme 7 is used in a synthesis like that of H269.

H290, H291 (Examples LIII, LIV and H294 (Example LV)

These syntheses are that of H269 modified to couple Ala or Phe to the Leu of the dipeptide isostere residue instead of His, or in the case of H294 simply using the Leu-R-Val isostere of H184, H185 in place of the hydroxy isostere in a synthesis otherwise as that of H269.

PART D

Examples with Isosteric Links Differing from the Preceding

The following examples are of renin-inhibiting peptide analogues containing isosteric links different from those described earlier herein. A table of structures, table 3, is followed by details of syntheses.

TABLE 3

| Ex. | Structure |
|---|---|
| LVI | Boc—Phe His Leu$\overset{NH_2}{\text{———}}$Val Ile His—NH$_2$<br>   8   9  10        11  12  13 |
| LVII | Boc—Phe His Leu$\overset{NH_2}{\text{———}}$Val Ile—NH—CH$_2$CH$_2$Ph<br>   8   9  10       11 12            13 |
| LVIII | Boc—Phe$\overset{Me}{\text{———}}$Phe Leu$\overset{NH_2}{\text{———}}$Val Ile—NH—CH$_2$CH$_2$—(2-pyridyl)<br>   8            9  10        11 12                   81 |
| LIX | Boc—Phe His Ast$^{(R)}$ Ile His—OH<br>   8    9   10    11   13 |
| LX | Boc—Phe His Ast$^{(S)}$ Ile His—OH<br>   8    9   10    11   13 |
| LXI | Boc—Phe His—N—CH($^i$Bu)—CH$_2$—NH—CH($^i$Pr)—CO—Ile His—OH<br>              \|<br>           CH$_2$CH$_2$NH$_2$<br>   8    9         10                               11        12  13 |
| LXII | 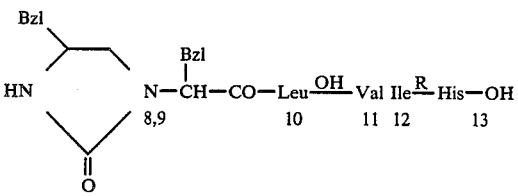 |
| LXIII | 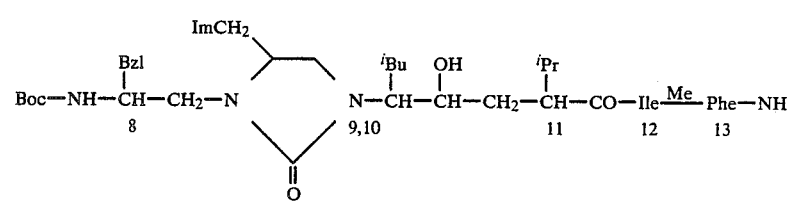 |
| LXIV | 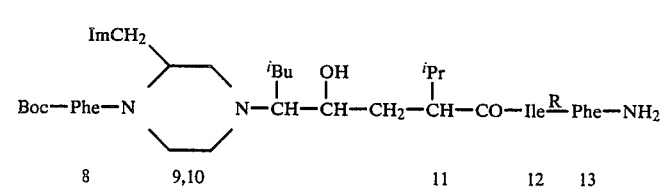 |

TABLE 3-continued

| Ex. | Structure |
|---|---|
| LXV | Boc—Phe His—N⟨iBu⟩⟨OH⟩—CH(iPr)—CO—Ile—$\overset{Me}{\phantom{-}}$—Phe—NH$_2$  (8  9  10,11  12  13) |
| LXVI | Boc—Phe Abu Leu—$\overset{OH}{\phantom{-}}$—Val Ile—N⟨Bzl⟩⟨=O⟩(ring)  (8  9  10  11  12  13) |

A synthesis route to the novel amino isostere -CH(NH$_2$)-CH$_2$- is illustrated in Scheme 12 below which shows the preparation of the protected Leu—$\overset{NH_2}{\phantom{--}}$—Val isostere 17. The latter can be incorporated into peptides, der the peptide backbone more resistant to attack by peptidases.

Scheme 12 (Examples LVI–LVIII)

Synthesis of protected amino isostere 11 is by reductive animation of the Boc-Leu-keto-Val isostere of Scheme 17 using ammonium acetate and sodium cyanoborohydride or by the following scheme:

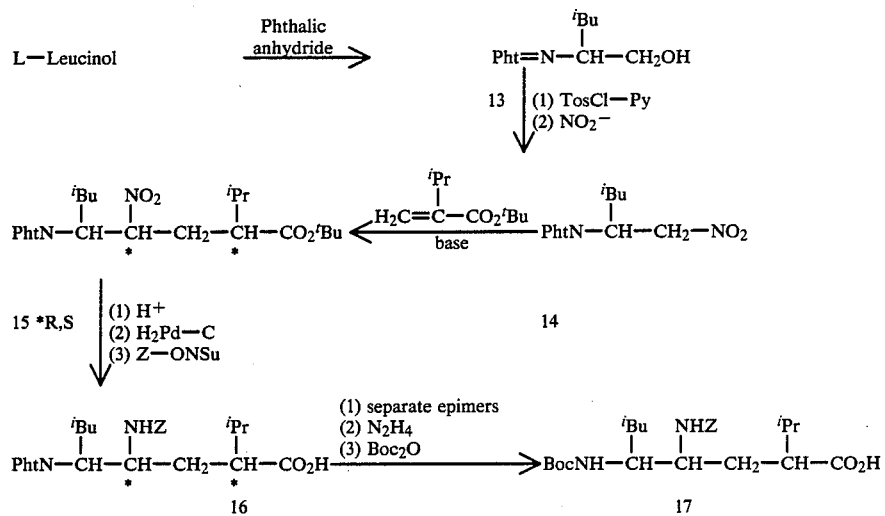

e.g. into the compounds of Examples LVI to LVIII by standard methods of peptide synthesis as described herein.

Correspondingly, Scheme 13 shows the synthesis of protected 3-amino-3-deoxy-statine, and in the analogues of Examples LIX, LX.

The compound of Example LXI is essentially a 'reduced' isostere of the kind described earlier herein but with an amino-ethyl substituent on the peptide nitrogen of residue 10.

The syntheses of the novel cyclic structures representing one or two residues in the backbone and present in the compounds of Examples LXII–LXVI are shown in Schemes 14–18. Again, incorporation into the final sequence is essentially by standard methods. These cyclic structures serve to stabilize the enzyme-bound conformation of each transition-state analogue, and to ren- As noted above the isostere 17 is incorporated into the full sequence of these examples by the standard methods of peptide synthesis, with the C-terminal free in the compound of Example LVI (His) and protected by -CH$_2$CH$_2$Ph and -CH$_2$CH$_2$-(2-pyridyl) in Examples LVII, LVIII(Ile). In the C-terminal sequence

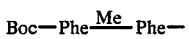

(Example LVIII), the methyl is on the peptide nitrogen of the Phe-Phe link.

Scheme 13 (Examples LIX, LX)

(A) Synthesis of protected 3-amino 3-deoxy-statine 39.

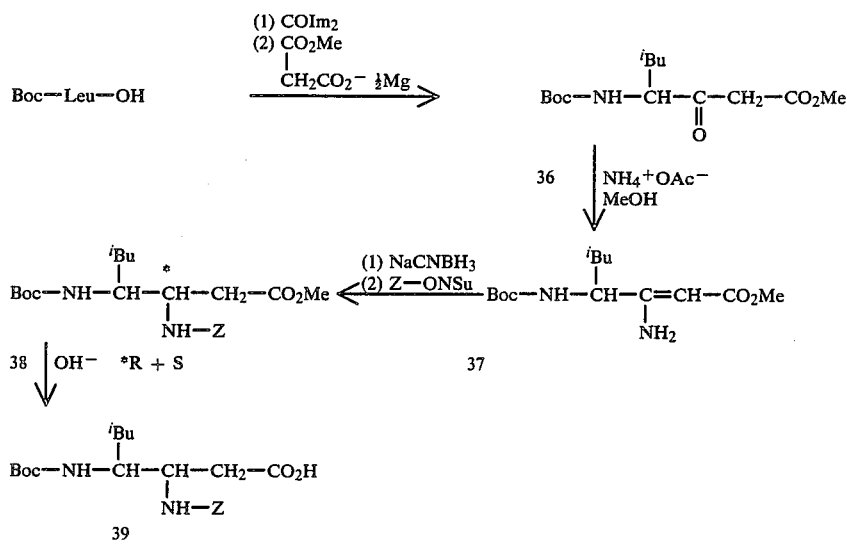

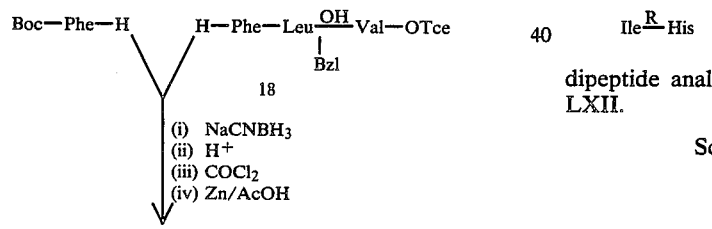

(B) Incorporation of 3-amino-3-deoxy-statine 39 into H-292 and 293.

39 is first coupled via DCCI/HOBt to H-Ile-His(-Bom)-OBzl, deprotected at the N-terminus with HCl-dioxan and then extended by stepwise coupling of Boc-His(Bom)-OH and Boc-Phe-OH. The protected peptide is separated into the two epimers differing in configuration at the carbon atoms bearing the amino substituent, and each one is deprotected by $H_2$/Pd-C in the presence of semicarbazide to give, respectively, H-292 (Example LIX) and H-293 (Example LX).

Scheme 14 (Example LXII)

-continued

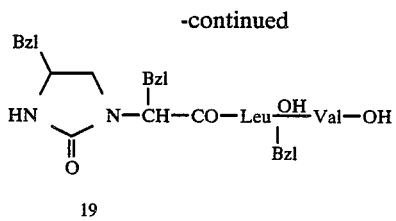

The analogue 18 is first made by the methods described herein, then converted to the cyclic form, as shown, before reaction with an Ile—$\overset{R}{\phantom{-}}$—His dipeptide analogue to give the analogue of Example LXII.

Scheme 15 (Example LXIII)

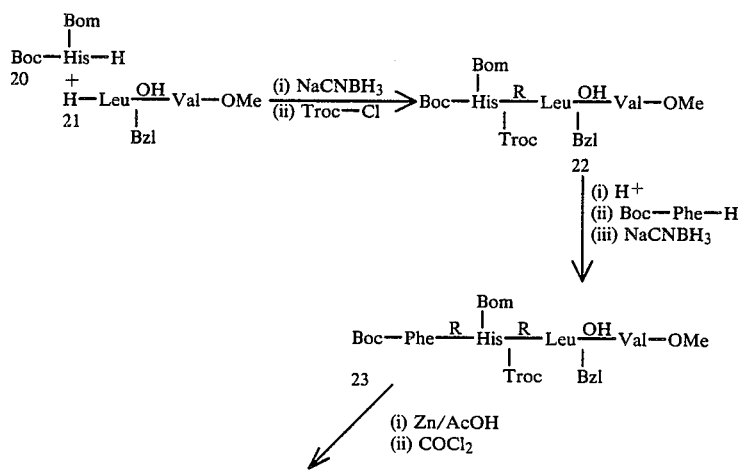

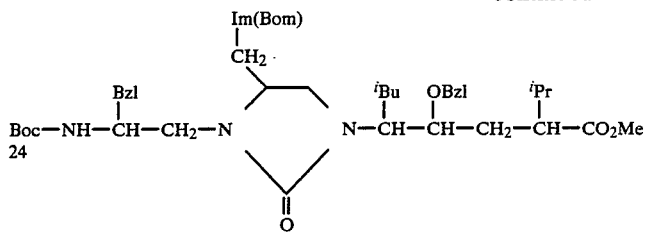

The synthesis above is followed to give compound 24 then the final amide protected residue Ile—Me—Phe—NH$_2$ attached, deprotecting as necessary to give the analogue of Example LXIII.

Scheme 16 (Example LXIV)

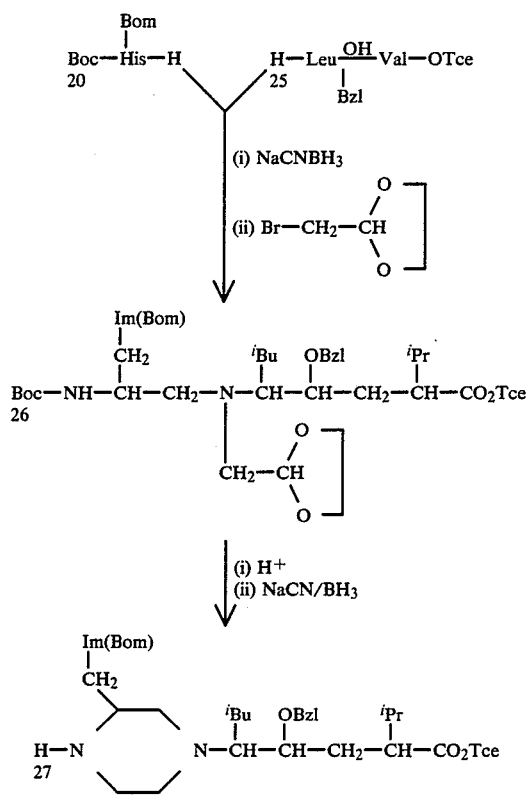

Compound 27 is synthesised as above then N-terminal Phe and C-terminal

Ile—R—Phe residues are attached by the methods described herein giving, after deprotection, the compound of Example LXIV.

Scheme 17 (Example LXV)

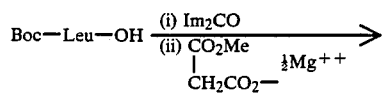

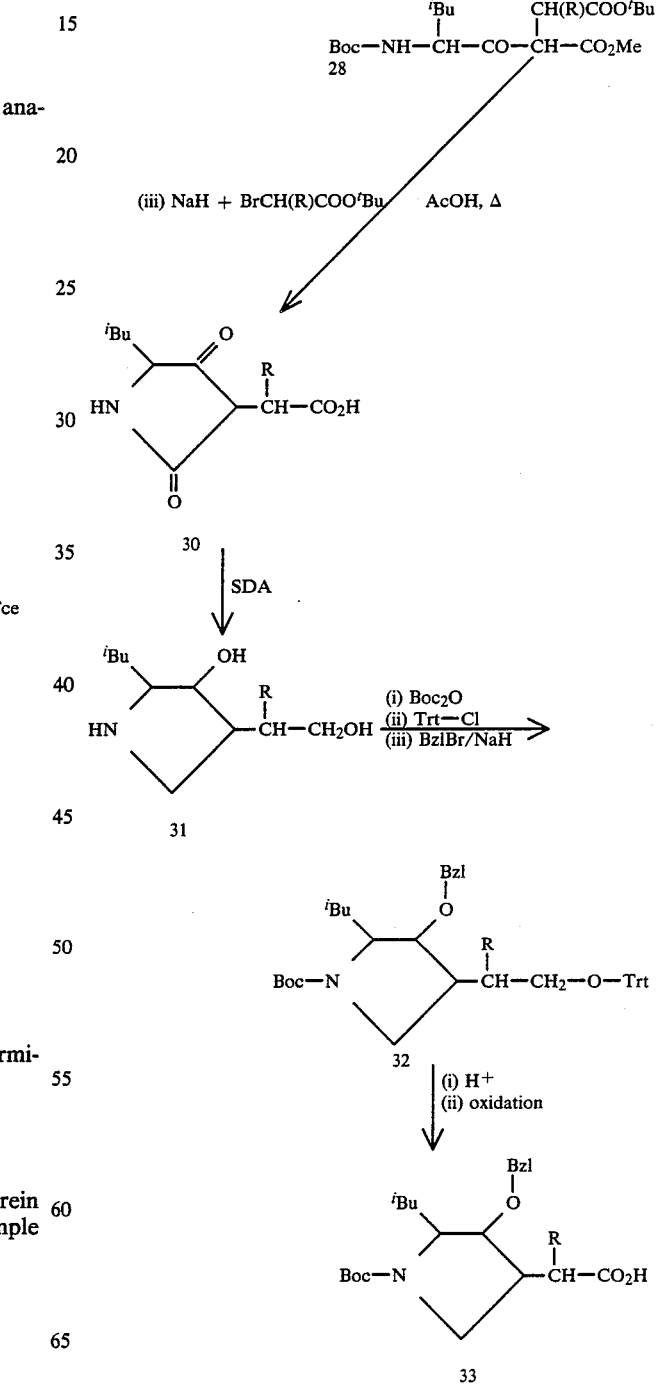

R = H in this instance

The compound 33 is synthesised as shown then N-terminal Phe-His and C-terminal

Ile —Me— Phe residues attached by the methods described herein giving after deprotection the analogue of Example LXV.

Scheme 18 (Example LXVI)

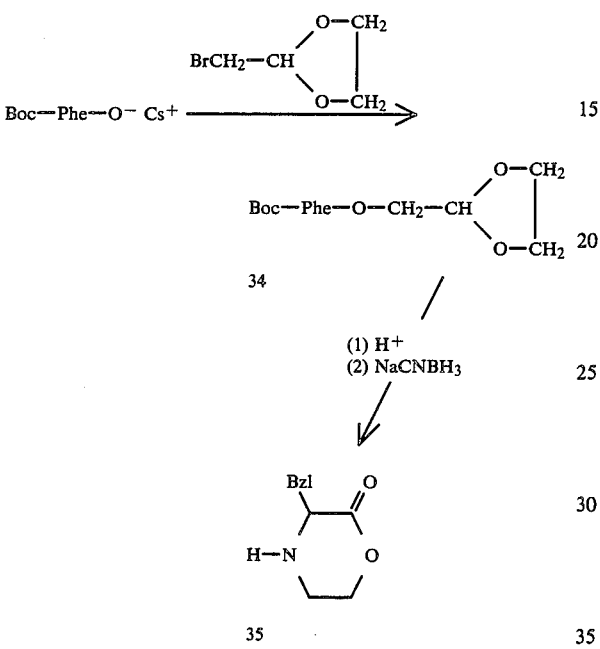

The Leu-OH-Val dipeptide analogue is made as given in detail earlier herein and the analogue of Example LXVI made by the methods given, compound 35 giving the C-terminal and the Phe-Abu the N-terminal residues.

TABLE 4

| ABBREVIATIONS | |
|---|---|
| Abu | 2-Aminobutyryl |
| Boc | t-Butyloxycarbonyl |
| Bom | π-Benzyloxymethyl |
| $^i$Bu | i-Butyl |
| $^s$Bu | s-Butyl |
| $^t$Bu | t-Butyl |
| Bzl | Benzyl |
| Im | Imidazol-4-yl |
| Leu —OH— Val | Hydroxy isostere, —CH(OH)CH$_2$— in place of —CONH— |
| Leu —K— Val | Keto isostere, —COCH$_2$— in place of —CONH— |
| Leu —Me— Val | N—Methyl peptide, —CONMe— in place of —CONH— |
| Leu —NH$_2$— Val | Amino isostere, —CH(NH$_2$)CH$_2$— in place of —CONH— |
| Me | Methyl |
| Ms | Methylsulphonyl |
| NBS | N—Bromosuccinimide |
| Ph | Phenyl |
| Pht | Phthaloyl |
| $^i$Pr | i-Propyl |
| SDA | Sodium dihydro-bis(2-methoxyethoxy)-aluminate |
| Tce | 2,2,2-Trichloroethyl |

TABLE 4-continued

| ABBREVIATIONS | |
|---|---|
| Thp | Tetrahydropyranyl |
| Troc | 2,2,2-Trichloro-ethoxycarbonyl |
| Trt | Triphenylmethyl |
| Ts | p-Toluenesulphonyl |
| Z | Benzyloxycarbonyl |
| Ast | 3-Amino-3-deoxy-statine H$_2$N—CH($^i$Bu)—CH(NH$_2$)—CH$_2$—COOH *(R) or (S) |
| DMECI | N—dimethylaminopropyl-N$^1$—diethyl carbodiimide |
| Pfp | Pentafluorophenyl |
| βNal | 3-(2-naphthyl)-alanine |
| αNal | 3-(1-naphthyl)-alanine |

Further 'Pro' or 'proline', outside the formula of specific individual compounds, includes substituted (particularly-OH substituted) proline and its ring homologues azetidine carboxylic acid (one-CH$_2$-less) and piperidine carboxylic acid (one-CH$_2$-more).

ACTIVITY IN VITRO

Preliminary activity test results in the human reninrenin substrate reaction in vitro are given, with comparative figures for the tetrapeptide analogue (III). The results are expressed as the IC$_{50}$ (the molar concentration required to cause 50% inhibition), and are given in part below in Table 5 and in part in the course of the specific description earlier (Tables 1, 2).

METHOD

The test results given herein are based on the methods described by J. A. Miller et al in Clinica Chimica Acta (1980) 101 5–15 and K. Poulsen and J. Jorgensen in J. Clin. Endocrinol. Metab. (1974) 39 816, and is based on the measurement, by radioimmunoassay, of angiotensin-I released from human renin substrate by human resin in human plasma. The inhibitor is dissolved in 0.01N HCl (10 μl) and added to hmman plasma (75 μl) containing EDTA, and angiotensin-I antibody (15 μl) in 3M-Tris/HCl buffer (pH 6.9).

After incubation at 37° C. for 0–120 minutes, the enzymic reaction is quenched by the addition of ice-cold 0.25M Tris/HCl buffer (pH 7.4) containing 0.01% of bovine serum albumin. 125I-labelled angiotensin-I is added, followed by equilibration at 4° C. for 48 hours. Free and bound ligand are separated by the addition of dextrancoated charcoal, and the amount of bound radio-ligand determined in a gamma counter.

TABLE 5

| | Results | |
|---|---|---|
| Analogue | | IC$_{50}$ |
| Example I | (H-76) | 1.0 μM |
| Example II | (H-79) | 17.0 μM |

TABLE 5-continued

| Analogue | | Results IC$_{50}$ |
|---|---|---|
| Example III | (H-78) | 1.5 μM |
| Example IV | (H-77) | 1.0 μM |
| Example V | (H-113) | 0.26 μM** |
| Example VI | — | * |
| Example VII | — | * |
| Example VIII | (H-110) | 1.3 μM |
| Example IX | (H-115) | 2.5 μM |
| Example X | (H-116) | 0.20 μM |
| Example XI | (H-108) | 0.05 μM |
| Example XII | (H-117) | 1.5 μM |
| Example XIII | (a) — | * |
| | (b) — | * |
| | (c) — | * |
| Example XIV | (H-104) | 0.0024 μM |
| Example XV | — | * |

*Preliminary indication of comparable activities.
**The corresponding non-isosteric peptide has for example been tested and shows a potency over three orders of magnitude less (IC$_{50}$ 400 μM) (Comparative) III 822 μM These results are most notable, showing a potency, in the reduction of renin activity remaining in the plasma in the presence of the analogue, several orders of magnitude greater than the previously proposed tetrapeptide analogue.

The potency of the compound of Example XIV is most especially notable, and it is an example of a "hydroxy" isostere. Comparing its IC$_{50}$ (0.0024 μM) with that of the corresponding Leu-reduced-Val isostere of Example V (0.26 μM) shows that high activity can be expected from this single change. Moreover the activity is highly specific, restricted to renin and not shown even in the closely related enzymes cathepsin D and renal acid protease.

ACTIVITY IN VIVO

Detailed activity tests have been conducted only in animals but indicate corresponding activity in man confirmed by preliminary studies in volunteers.

In the in vivo studies compounds are infused into normal, conscious sodium-depleted dogs at rates of 0.01, 0.1, 1 and 10 mg/kg/hr. A maximum fall in blood pressure plasma renin (PR) angiotensin-I (AI) and angiotensin-II (AII) levels is obtained within 10 minutes at doses of 1 and 10 mg/kg/hr. When the infusion is stopped, blood pressure returns to baseline levels 30 minutes after the 1 mg/kg/hr. doses, but more slowly after the 10 mg/kg/hr. doses. Results of the same kind have been obtained in the baboon, in six animals, as a close model of man.

USES IN MAN

In use of the compounds, a person suffering from hypertension is for example given a nasal instillation preparation of 0.01 to 1 mg/kg body weight of the compound per dose, for example three times a day. Clinically significant maintained reduction of the hypertension is a positive indication of hypertension amenable to treatment by the method of the invention. The method may be similarly applied to patients in heart failure. In both the hypertension and the heart failure instances the plasma-renin may or may not be above normal.

Longer term, persons diagnosed as suffering from amenable hypertension as above are treated by means of a continuing course of one or more of the compounds.

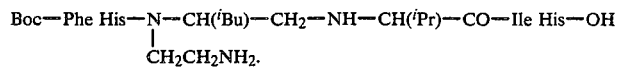
35. The compound
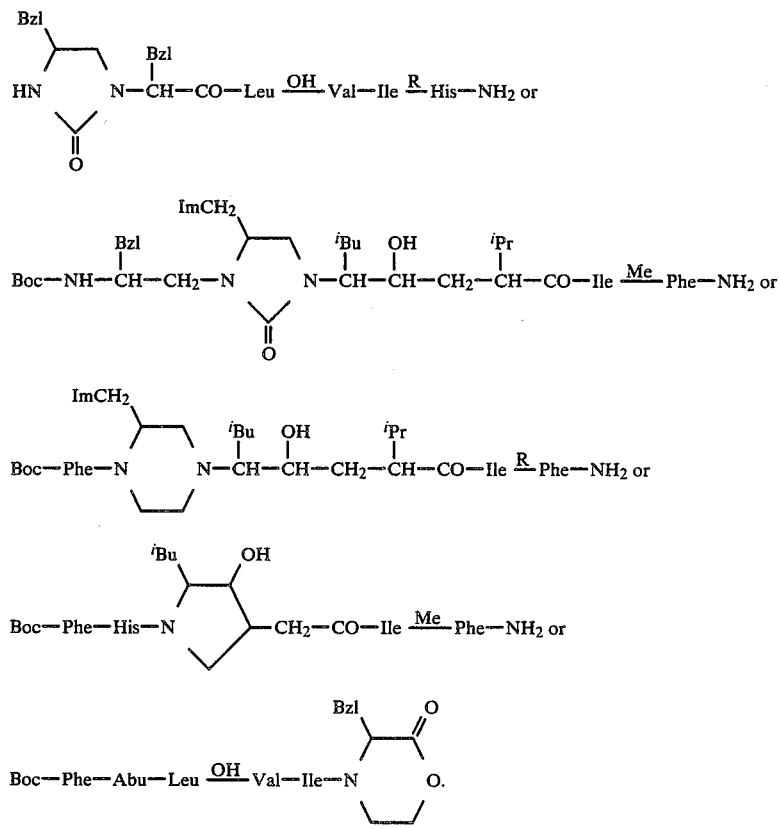

We claim:

1. Compounds of the general formula $$X-D-E-A-B-Z-W \quad (XIV)$$
$$\phantom{X-}8\phantom{-}9\phantom{-}10,11\phantom{-}12\phantom{-}13$$

where
X = H or an N-protecting group or groups
D = absent or is Phe, αNal, βNal, Tyr, His, Trp or cyclohexyl alanyl as such or reduced at carbonyl
E = absent or is His Ala, Phe, Tyr, Trp, 2-aminobutyrl or α, δ-diaminovaleryl as such or Nα-alkylated or reduced at carbonyl A = (a) 
$$\begin{array}{c} R^4 \ R^1 \ \ R^2 \\ | \ \ | \ \ \ | \\ -N-C-M-C-G^1- \\ | \ \ \ \ \ \ | \\ R^5 \ \ \ \ R^6 \end{array}$$ where $R^4$, $R^5$ and $R^6$ the same or different =
(i) H or
(ii) alkyl or
(iii) $-(CH_2)_n-OH$ or $-(CH_2)_n-NH_2$ when n = 2, 3, 4
$G^1$ (and $G^2$ appearing below) =
(i) $-CH_2-(CH_2)_n-$ or
(ii) $-(CH_2)_n-CO-$ or  } where n = 0-3
(iii) $-CO-(CH_2)_n-$
$R^1$ and $R^2$, the same or different =
H, alkyl, ArCH$_2$ or cyclohexyl-methyl
M = (i) $-CH(OH)-(CH_2)_n-$ or
(ii) $-CH(NH_2)-(CH_2)_n-$ or
(iii) $-CH_2-(CH_2)_n-$ or
(iv) $-CO-(CH_2)_n-$ or   } where n = 0-2
(v) $-(CH_2)_n-N(R^7)-$, where $R^7 = X$
(vi) $-CH(NH_2)-(CH_2)_n-CO-NH-$
with the provisos (I) that when M = (i), (iii) or (iv) and n = 1 then two three or four, and when M = (v) and n = 1 then three or four, of D, E, B and Z are present
(II) when M = (i), (ii) or (iv) then $R^5$ and $R^6$ are H and when M = (iii) or (v) then if one of $R^4$, $R^5$, $R^6$ and $R^7$ is said group $-(CH_2)_n-OH$ or $-(CH_2)_n-NH_2$ the others the same or different, are H or alkyl
or A = (b) 
$$\begin{array}{c} R^1 \\ \diagdown \\ CH-Y^1 \ \ \ R^2 \\ / \ \ \ \diagdown \ | \\ -N \ \ \ \ \ \ CH-CH-G^2- \\ \diagdown \ \ / \\ G^1 \end{array}$$ where $R^1$, $R^2$ and $G^1$, $G^2$, the same or different, are as defined above and
Y = (i) $-CO-$ or
(ii) $-CH_2-$ or
(iii) $-CH(OH)-$ or
(iv) $-CH(NH_2)-$ or
(v) $-CH_2-NR^3-$ ($R^3$ as above)
B = absent or is Val, Leu, Ile Phe either as such or Nα-alkylated and/or reduced at carbonyl
Z = absent or is His, Phe, Tyr, or cyclohexyl alanyl and is either as such or Nα-alkylated and/or reduced at carbonyl
W = (a) $-OH$,
(b) $-OR^3$    } $R^3$ as above
(c) $-NH_2$, $-NHR^3$, $-N(R^3)_2$ (d) $-N\underset{\smile}{\phantom{n}}$ where N is part of a heterocyclic ring optionally substituted with R$_3$ or R$^3$CH$_2$—groups at one or more positions
or -continued

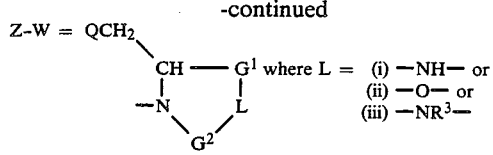

and R³ and G¹ and G², the same or different, are as defined above and

Q = (i) H or
(ii) C₁₋₄ alkyl or
(iii) aryl or
(iv) imidazol-4-yl- or indol-3-yl all compounds being in free form or protected at one or more remaining peptide, carbonyl, amino or other reactive groups including peptide nitrogen or in salt form at amino imidazole or carboxyl groups in particular as physiologically acceptable acid addition salts at basic centres.

2. Compounds according to claim 1 wherein for any value of n in the definition of M, when M=(i), (iii) or (iv) then two, three or four and when M=(v) then three or four of said residues are present.

3. Compounds according to claim 1, wherein said group X is

| | |
|---|---|
| (a) R³—(CH₂)ₙ, where n = 0–4, | or |
| (b) R³—CO— | or |
| (c) R³—O—CO— | or |
| (d) R³—(CH₂)ₙ—CO— | or |
| (e) R³—(CH₂)ₙ—O—CO | or where n = 0–5 |
| (f) R³—O—(CH₂)ₙ—CO— | or |
| (g) R³SO₂— | or |
| (h) (R³)₂—N—CO— | |

In (a)–(h), R³ =
(i) H (except in (c)) or
(ii) alkyl or
(iii) cycloalkyl C₃₋₇ or
(iv) bicycloalkyl or tricycloalkyl or
(v) aryl or aryl alkyl.

4. Compounds according to claim 1, wherein R¹ and R² are selected from
(i) alkyl or
(ii) ArCH₂ or
(iii) cyclohexyl-methyl) or
(iv) H.

5. Compounds according to claim 1 wherein said group W=

| | |
|---|---|
| —OH | (a) |
| —OR³ | (b) |
| —NH₂, —NHR³, —N(R³)₂ } R³ as above | (c) |
| 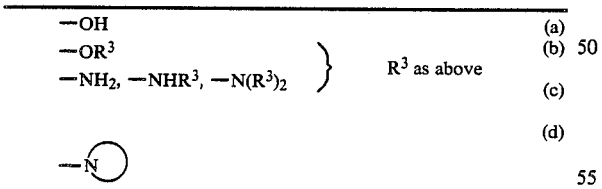 | (d) | where N is part of a heterocyclic ring optionally substituted with R³ or CH₂- groups at one or more positions.

6. Compounds according to claim 1 in the form of compounds in which, when one or more of the peptide bonds of the chain is represented by a 'reduced' isostere, the N atom of such isostere and the preceding or succeeding N atom in the chain are linked by a moiety as defined for G¹ and giving a five or six membered ring, and together further with compounds in which the above residues are present with further, N- or C-terminal, aminoacyl or aminoacyl analogue residue(s) interposed between X and D, J being His residue, and compounds in which one or more remianing peptide links have been replaced by analogues M.

7. Compounds according to claim 1, wherein Y-Pro is inserted between X and D, Y being D- or L- His residue and Pro being as such or substituted by OH or replaced by pGlu.

8. Compounds according to claim 1, wherein W is serine or L- or D- lysine, arginine residue as such or in amide form, substituted amide form or ester form or an amino alcohol residue derived therefrom as such or protected in ester or ether form.

9. The compounds of claim 1, wherein, in M, n=1.

10. The compounds of claim 1, or 9 wherein M=-CH(OH)-(CH₂)ₙ-.

11. The compounds of claim 1, or 9, wherein M=-CH(NH₂)-(CH₂)ₙ-.

12. The compounds of claim 1, or 9, wherein M=-CH(NH₂)-(CH₂)ₙ-CO-NH-.

13. The compounds of claim 1, wherein A=

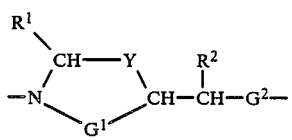

as defined herein.

14. The compounds of any of claims 1 or 9, wherein in A, R⁵ and R⁶ are hydrogen.

15. Compounds of the general formula:

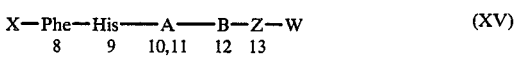

where Phe and His are optional but are not both absent when A has the 'reduced' link below X = H or an N—protecting group;

A = 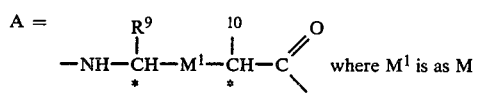 where M¹ is as M above or a 'reduced' —CH₂—N— or 'keto'
                                    |
                                    R¹¹

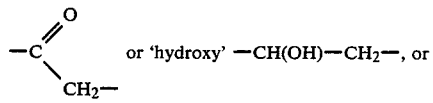 or 'hydroxy' —CH(OH)—CH₂—, or

'hydrocarbon' —CH₂—CH₂— isostere bond where the configuration at asymmetric centres is either R or S, where in the hydroxy isostere the hydroxy group may be present as such or protected in ether or ester form and where R⁹ and R¹⁰, the same or different = an amino-acid side chain;

R¹¹ = —H or an N—protecting group;
B = D- or L- Val, Leu, or Ile;
Z = D- or L- Tyr, Phe or His residue; and
W = (i) —OH or
(ii) —NH₂ or
(iii) a serine or basic amino-acyl residue; or
Z + W = an alcohol derived from L- or D- Tyr, Phe, His residue;

such compound being in the above form or modified by isosteric replacement of one or more remaining peptide bonds and further being in free form or in protected form at one or more remaining amino or amide, nitrogen, carboxyl, hydroxy or other reactive groups, or in salt form at amino imidazole or carboxyl groups.

16. Compounds according to claim 15, wherein Phe and His are in substituted form, Phe by OH F Cl Br or Me, at the 4-position, or His by Me; or Phe is replaced by Tyr, or His by spinacin.

17. Compounds according to claim 15, wherein group X is an acyl group acetyl, pivaloyl, t-butyloxycarbonyl (Boc), benzoyl or lower alkyl (primarily $C_1$-$C_5$); or an L- or D-amino-acyl residue, which may itself be N-protected similarly and in particular may be Gly or D- or L-Pro, Val or Ile.

18. Compounds according to claim 15, wherein said hydroxy isostere A is in ether -$OR^{12}$ or ester

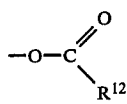

form where $R^{12}$ is as given under W below.

19. Compounds according to claim 15, wherein in A, $R^9$ and $R^{10}$, the same or different=isopropyl, isobutyl, benzyl or other amino-acid side chain.

20. Compounds according to claim 15 wherein $R^{11}$ is lower alkyl ($C_1$-$C_5$), or t-butyloxycarbonyl or benzyloxycarbonyl as such or ring substituted, or aryl sulphonyl e.g. -$SO_2Ph$ or -$SO_2$-$C_6H_4CH_3(p)$, or formyl.

21. Compounds according to claim 15, wherein when W is -OH it is in protected ester form as -$OR^{12}$ where $R^{12}$=lower alkyl primarily $C_1$-$C_5$ and $^tBu$, or cycloalkyl primarily $C_3$-$C_7$, or other ester forming group.

22. Compounds according to claim 15, wherein W is -$NH_2$, it is in protected amide form as -$NHR^{13}$ or -$N(R^{13})_2$ (where $R^{13}$=an N-protecting group, and $(R^{13})_2$=two such or e.g. cycloalkyl, primarily $C_3$-$C_7$) or as -NH-$(CH_2)_n$-$Q^1$ or -$NR^{13}$-$(CH_2)_n$-$Q^1$ (where n=2 to 6 and $Q^1$=$NH_2$ or

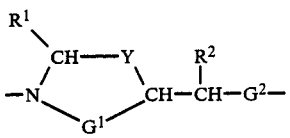

and wherein G is hydrogen.

23. Compounds according to claim 15, wherein said serine or basic amino acyl residue W is an L- or D-serine or L- or D-lysine or arginine.

24. The compounds of claim 15, wherein A contains the 'hydroxy' isostere bond.

25. Compounds as in claim 15 but having in place of A the group

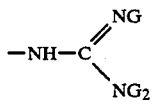

where M is as in claim 1 and $R^1$ and $R^2$ are as in claim 15.

26. The compounds of claim 24 wherein, in M, n=1.

27. The compounds of claim 24 or 25, wherein M=-CH(OH)-$(CH_2)_n$-.

28. The compounds of claim 24 or 25 wherein M=-CH($NH_2$)-$(CH_2)_n$-CO-NH-.

29. Compounds as in claim 15 but having in place of A the group

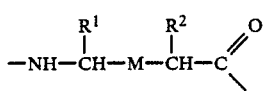

as defined in claim 1.

30. The compound

H—Leu $\xrightarrow{OH}$ Val Ile His Lys—OH or

Boc—Leu $\xrightarrow{OH}$ Val Ile His—OH or

H—Leu $\xrightarrow{OH}$ Val Ile His—OH or

Boc—His Leu $\xrightarrow{OH}$ Val Ile His—OH or

H—His Leu $\xrightarrow{OH}$ Val Ile His—OH or

Boc—Phe His Leu $\xrightarrow{OH}$ Val Ile His—OH or

H—Phe His Leu $\xrightarrow{OH}$ Val Ile His—OH or

Boc—Phe His Leu $\xrightarrow{OH}$ Gly Ile His—OH or

Boc—Phe His Leu $\xrightarrow{OH}$ Val Ile Phe—OMe or

Boc—Phe His Leu $\xrightarrow{OH}$ Val Ile—OMe or

Boc—Phe His Leu $\xrightarrow{OH}$ Val Ile His—OMe or

Boc—Phe His Leu $\xrightarrow{K}$ Val Ile His—OH or

Boc—Phe Ala Leu $\xrightarrow{OH}$ Val Ile His—OH or

Boc—Phe Phe Leu $\xrightarrow{OH}$ Val Ile His—OH.

31. The compound

Boc—Phe His Leu $\xrightarrow{R}$ Val Ile His—OH.

32. The compound
Boc-Phe His Ast$^{(R)}$ ILe His-OH
Boc-Phe His Ast$^{(S)}$ Ile His-OH.

33. The compound

Boc—Phe His Leu$\xrightarrow{NH_2}$ Val Ile His—$NH_2$ or

Boc—Phe His Leu$\xrightarrow{NH_2}$ Val Ile—NH—$CH_2CH_2$Ph or

Boc—Phe$\xrightarrow{Me}$Phe Leu$\xrightarrow{NH_2}$Val Ile—NH—$CH_2CH_2$-(2-pyridyl).

34. The compound